(12) United States Patent
Demers et al.

(10) Patent No.: US 7,291,839 B1
(45) Date of Patent: Nov. 6, 2007

(54) SUBCENTIMETER RADIATION DETECTION AND FREQUENCY DOMAIN SPECTROSCOPY

(75) Inventors: Joseph R Demers, Glendale, CA (US); Ronald T. Logan, Jr., Pasadena, CA (US)

(73) Assignee: Emcore Corporation, Somerset, NJ (US)

( * ) Notice: Subject to any disclaimer, the term of this patent is extended or adjusted under 35 U.S.C. 154(b) by 191 days.

(21) Appl. No.: 11/121,350

(22) Filed: May 3, 2005

Related U.S. Application Data

(60) Provisional application No. 60/568,049, filed on May 3, 2004.

(51) Int. Cl.
*G01J 5/02* (2006.01)
(52) U.S. Cl. .................. 250/341.1; 250/338.1
(58) Field of Classification Search ............. None
See application file for complete search history.

(56) References Cited

U.S. PATENT DOCUMENTS

| | | | | |
|---|---|---|---|---|
| 5,379,309 | A * | 1/1995 | Logan, Jr. ............. | 372/18 |
| 5,623,145 | A * | 4/1997 | Nuss ...................... | 250/330 |
| 6,348,683 | B1 * | 2/2002 | Verghese et al. ...... | 250/214.1 |
| 6,849,852 | B2 * | 2/2005 | Williamson ............ | 250/341.6 |
| 6,865,014 | B2 * | 3/2005 | Ciesla et al. .......... | 359/326 |
| 7,174,037 | B2 * | 2/2007 | Arnone et al. ......... | 382/128 |
| 2006/0255277 | A1 * | 11/2006 | Cole et al. ............. | 250/341.1 |

OTHER PUBLICATIONS

Linde, Characterization of the Noise in Continuously Operating Mode-Locked Lasers, 1986, Applied Physics B, vol. 39, p. 201-217.

Demers et al, Spectral Purity and Sources and Noise in Femtosecond-Demodulation Terahertz Sources Driven by Ti: Sapphire Mode-Locked, Apr. 2001, IEEE Journal of Quantum Electronics, vol. 4, p. 595-605.

Shillue et al, Millimetre Wave Generation Using an Optical Comb Generator with Optical Phase-Locked Loops, Oct. 2002, ALMA memo #439.

Sukhotin et al, Picosecond Photocarrier-Lifetime in ErAs:InGaAs at 1.55 μm, Nov. 2003, Applied Physics Letters, vol. 83, No. 19, p. 3921-3923.

Brown et al, Coherent Millimeter-wave Generation by Heterodyne Conversion in Low-Temperature-Grown GaAs Photoconductors, Feb. 1993, Jornal of Applied Physics, vol. 73, No. 3, p. 1480-1484.

(Continued)

*Primary Examiner*—David Porta
*Assistant Examiner*—Frederick F Rosenberger
(74) *Attorney, Agent, or Firm*—Pritzkau Patent Group LLC

(57) ABSTRACT

A system, method and detection arrangement for investigation of a sample are described. A laser illumination arrangement generates (i) a source laser energy that is incident on a source to cause emission of subcentimeter radiation, at least a portion of which interacts with the sample to serve as a sample influenced radiation incident on a detector and (ii) a detector laser energy that is incident on the detector to produce an optical component of the detector laser energy offset with respect to a corresponding optical component of the source laser energy so that the collective energy at the detector generates an electrical output signal responsive to the sample influenced radiation. In another aspect, a detection arrangement is used with at least two continuous wave lasers for causing the detector body to respond in a way which produces a frequency down-converted signal from an incident electromagnetic radiation.

41 Claims, 11 Drawing Sheets

OTHER PUBLICATIONS

McIntosh et al, Terahertz Photomixing with Diode Lasers in Low-Temperature-Grown GaAs, Dec. 1995, Applied Physics Letters, vol. 67, No. 26, p. 3844-3846.

McIntosh et al, Terahertz Measurements of Resonant Planar Antennas Coupled to Low-Temperature-Grown GaAs Photomixers, Dec. 1996, Applied Physics Letters, vol. 69, No. 24, p. 3632-3634.

Verghese et al, Optical and Terahertz Power Limits in the Low-Temperature-Grown GaAs Photomixers, Nov. 1997, Applied Physics Letters, vol. 71 No. 19, p. 2743-2745.

Sukhotin et al, Photomixing and Photoconductor Measurements on ErAs/InGaAs at 1.55 μm, May 2003, Applied Physics Letters, vol. 82, No. 18, p. 3116-3118.

Brown et al, Photomixing up to 3.8 THz in Low-Temperature-Grown GaAs, Jan. 1995, Applied Physics Letters, vol. 66, No. 3, p. 285-287.

Smith et al, Subpicosecond Photoconducting Dipole Antennas, Feb. 1988, vol. 24, No. 2, p. 255-260.

Siegel, Terahertz Technology, Mar. 2002, IEEE Transactions on Microwave Theory and Techniques, vol. 50, No. 3, p. 910-928.

Schoof et al, Reducing the Linewidth of a Diode Laser Below 30 Hz by Stabilization to a Reference Cavity with a Finesse Above $10^5$, Oct. 2001, Optics Letters, vol. 26, Issue 20, pp. 1562-1564.

Lombardi et al, Time and Frequency Measurements Using the Global Positioning System, Cal Lab, Jul. 2001, pp. 26-33.

* cited by examiner

SUBCENTIMETER RADIATION DETECTION AND FREQUENCY DOMAIN SPECTROSCOPY

RELATED APPLICATION

The present application claims priority from U.S. Provisional Patent Application Ser. No. 60/568,049 entitled COMPACT SUBMILLIMETER WAVE SOURCES AND DETECTORS FOR SPECTROSCOPIC APPLICATIONS, filed on May 3, 2004, which is incorporated herein by reference in its entirety.

BACKGROUND OF THE INVENTION

The present invention is generally related to the field of applications that employ terahertz radiation and, more particularly, at least to the detection of subcentimeter radiation in the frequency domain. Still more particularly, a system is described for investigation of the properties of a sample of matter using subcentimeter radiation in the frequency domain.

While the prior art includes a number of approaches for the production of terahertz energy, there are considered to be a limited number of approaches with respect to detection and analysis of such radiation. One prior art method for the detection of submillimeter radiation utilizes a Helium Bolometer. Such a device has a very slow response and requires liquid Helium to function. These characteristics make it unsuitable for a large number of applications. Another prior art method uses a high frequency mixer diode in conjunction with a multiplied sub-millimeter source to perform downconversion of the subject radiation to a lower frequency range. This latter technique is limited, however, since such mixer diodes are typically provided in waveguide structures that are characterized by a significantly limited bandwidth of operation. Still another detection method performs detection of sub-millimeter radiation in a semiconductor material using time domain analysis of sub-millimeter pulses.

It is noted that the terms THz and sub-millimeter are often used in the prior art to refer to at least a segment of the energy that is of interest herein. The term sub-millimeter (submm) may be considered as the more technically accurate of the two terms since it can be considered to refer to the wavelength in a vacuum as being less than or equal to 1 millimeter. While no precise definition is available, in the literature it appears that when the term "THz" is used, it refers generally to radiation in the frequency range of 0.1 THz to 10 THz. Since 1 mm is about 300 GHz, the "THz region" of the current technological parlance is really more than sub-mm. Based on these considerations, Applicants have adopted the term sub-centimeter (sub-cm) (~30 GHz) wherein the wavelength in a vacuum is less than or equal to approximately 1 centimeter.

One approach, in a paper by Smith, Auston and Nuss, describes the use of a photoconducting dipole antenna for purposes of generating and sensing terahertz radiation. As described, a balanced colliding pulse mode-locked laser, driven by an argon laser, is used for purposes of generating short duration optical pulses. The pulsed output is split into two beams of equal intensity. One beam is delivered to a transmitting antenna so as to excite the transmitting antenna to emit a burst of terahertz energy. A receiving antenna is spaced away from the transmitting antenna for receiving the burst of terahertz energy. The other beam of pulsed laser energy is first delayed such that it arrives at the receiving antenna at the same time as the burst of terahertz energy. The delayed laser pulsed energy thereby serves to gate the receiving antenna at the time of arrival of the terahertz pulse. Unfortunately, the gate pulse, at the receiving antenna, will have a duration that is far shorter than the received terahertz energy, since the latter will be subject to dispersion in traveling from the transmitter antenna to the receiver antenna. Thus, a very small sample of the dispersed terahertz energy will be received. Although one of these gated samples of the dispersed terahertz energy is relatively useless standing on its own, since it merely represents a very limited portion of an overall domain response, Smith et al. recognize a technique for obtaining useful information from a plurality of such pulses that are delayed by different amounts so as to reconstruct an overall time domain or temporal response. It is noted that this sort of analysis is nontrivial. Further, substantial complexity is introduced with respect to appropriately timing the gating pulse.

Accordingly, the approach of Smith et al. allows one, after collecting a significant number of time-gated samples, to perform a Fourier transform of the overall temporal response whereby to obtain a frequency response. Since achieving the resolution required for molecular spectroscopy would require a delay line of over a thousand meters, such a time domain based response is considered to be unsuitable. Further, the burst of terahertz energy emitted by the transmitting antenna is spread across a relatively wide bandwidth whereas, in a single, narrow bandwidth component, the radiated subcentimeter power would be greater, leading to improved signal-to-noise ratios for spectroscopic applications.

A logical extension of the work of Smith et al., therefore, is the application of what is referred to in the prior art as "terahertz time domain spectroscopy" wherein a sample to be investigated is placed between the source of terahertz energy and the detector. U.S. Pat. No. 5,623,145, issued to Nuss, represents the extension of this work by one of the co-authors of the Smith et al. article. In particular, the Nuss patent reportedly teaches time domain spectroscopy for the purpose of performing imaging. Applicants see no substantive change with respect to the overall gating technique.

The prior art has continued to develop with respect to terahertz time domain spectroscopy as demonstrated, for example, by U.S. Pat. No. 6,865,014. It is submitted, however, that no fundamental change in the basic operation of these systems has occurred in which the detector is gated by a delayed pulse. In particular, it is submitted that there is at least a need for a new scheme for detection of terahertz energy which avoids the difficulties encountered in the approach of time domain analysis. Moreover, frequency response is the objective of spectroscopy, as opposed to first obtaining a temporal response. Accordingly, time domain spectroscopy is submitted to be an indirect, limited and circuitous approach to spectroscopy, when frequency domain response is the objective in the first instance.

The present invention is submitted to sweep aside the foregoing difficulties and concerns while providing still further advantages.

SUMMARY OF THE DISCLOSURE

A system, associated method and associated detection arrangement for investigation of a sample are described. In one aspect of the invention, a source arrangement is employed having a source frequency response. A detector arrangement is provided in a positional relationship with the source arrangement such that the sample is located in relation thereto, and the detector arrangement includes a detector frequency response. A laser illumination arrangement generates (i) a source laser energy that is incident on the source arrangement, based on the source frequency response, in a way which causes the source arrangement to emit subcentimeter radiation, at least a portion of which subcentimeter radiation interacts with the sample and, thereafter, at least some of the portion of the subcentimeter radiation serves as a sample influenced radiation that is incident on the detector arrangement, based on the positional relationship, and (ii) a detector laser energy that is incident on the detector arrangement and coordinated with the source laser energy in a way which produces at least one optical component of the detector laser energy that is offset with respect to a corresponding optical component of the source laser energy so that the detector laser energy and the sample influenced radiation interact, based on the detector frequency response, in a way which at least generates an electrical output signal across the detector arrangement such that the electrical output signal is responsive to the sample influenced radiation.

In another aspect of the invention, an apparatus and associated method are described for detecting a radio frequency radiation. A detector is provided having a detector frequency response so that the radio frequency radiation is incident on the detector arrangement. An illumination arrangement continuously illuminates the detector arrangement with laser radiation that is produced by at least two continuous wave lasers for causing the detector arrangement to respond, based on the detector frequency response, in a way which causes the laser radiation to interact with the subcentimeter radiation to produce a frequency down-converted signal from the subcentimeter radiation.

DESCRIPTIONS OF THE DRAWINGS

The present invention may be understood by reference to the following detailed description taken in conjunction with the drawings briefly described below.

DETAILED DESCRIPTION

The following description is presented to enable one of ordinary skill in the art to make and use the invention and is provided in the context of a patent application and its requirements. Various modifications to the described embodiments will be readily apparent to those skilled in the art and the generic principles herein may be applied to other embodiments. Thus, the present invention is not intended to be limited to the embodiment shown but is to be accorded the widest scope consistent with the principles and features described herein including alternatives, modifications and equivalents, as defined within the scope of the appended claims. It is noted that the drawings are not to scale and are diagrammatic in nature in a way that is thought to best illustrate features of interest. Further, like reference numbers are applied to like components, whenever practical, throughout the present disclosure. Descriptive terminology such as, for example, uppermost/lowermost, right/left, front/rear and the like has been adopted for purposes of enhancing the reader's understanding, with respect to the various views provided in the figures, and is in no way intended as been limiting.

Figure 1:
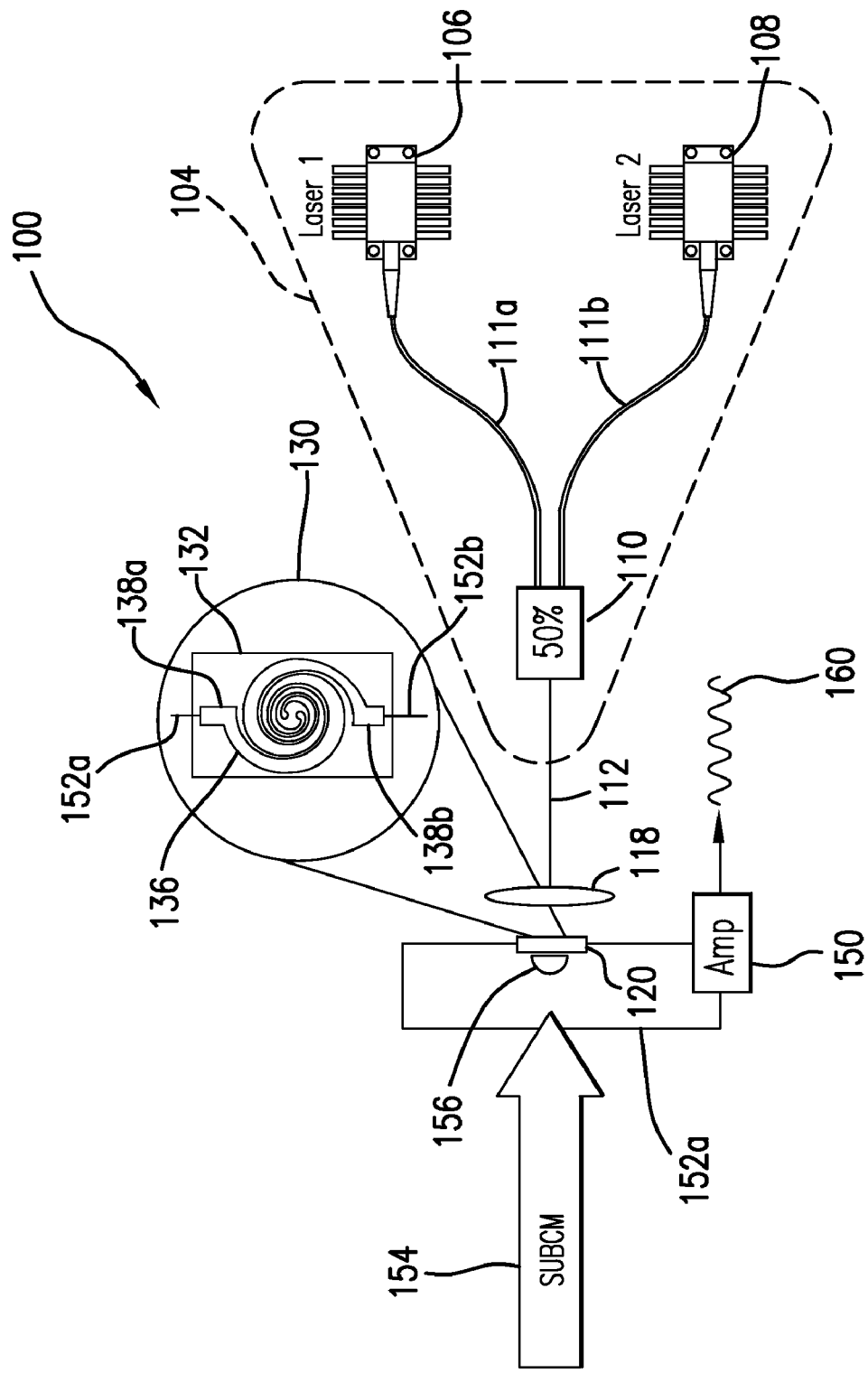
FIG. 1 is a diagrammatic plan view of a highly advantageous detection arrangement for use in detecting subcentimeter radiation.

Turning now to FIG. 1, a detection arrangement is generally indicated by the reference number 100 for use in detecting what is referred to hereinafter as "subcentimeter" radiation or energy. The term subcentimeter radiation is intended to encompass radiation with wavelengths less than or including 1 centimeter, including millimeter and sub-millimeter wave electromagnetic energy, as well as what is typically referred to as "terahertz" radiation in the current popular vernacular. Detection arrangement 100 is considered to be highly advantageous for reasons to be made evident below.

Still referring to FIG. 1, detection arrangement 100 includes a detection laser energy source 104 within a dashed line. Laser energy source 104, in the present example, includes a first laser 106 and a second laser 108 having outputs that are coupled to a combiner 110 using a pair of optical cables 111a and 111b. Combiner 110 provides an output 112 that is made up, at least approximately, of equal energy from each of lasers 106 and 108. Output 112 is carried by another optical cable such that the combined laser energy, which may be referred to as detector laser energy, is incident on a lens 118, which serves to focus the detector laser energy onto a detector 120. Thus, the laser energy source continuously illuminates the detector body with laser radiation that is produced by at least two continuous wave lasers. Lens 118 can be formed from any suitable optical material. Detector 120 is shown in a side view and, further enlarged, in a plan view within a circle 130. Detector 120 includes a detector body 132 which may be formed from any suitable material including, but not limited to Low Temperature Grown Gallium Arsenide, LTG GaAs. An antenna 136 is formed on the detector body, for example, by sputtering gold onto the detector body in the desired spiral configuration, as further described below. The detector body includes a detector frequency response which influences interaction with the laser energy. It is noted that the detector arrangement, configured as shown, may be referred to as an LTG GaAs Photo-Conductive Switch or Detector PCS.

For purposes of the examples herein, it is noted that the detector body is considered to include antenna 136 and any frequency response effects that are attributable to the antenna. Applicants have recognized that the antenna structure of Brown et al. [see reference 4 below] is suitable for use in this detector application, although Brown uses the antenna for purposes of photomixing to produce terahertz energy. The antenna is characterized as a three-turn self-complementary spiral antenna having a center interdigitated-electrode photomixer structure. Other antenna structures may also be found to be useful. Spiral antenna 136, in the present example, includes opposing connection points 138a and 138b. An amplifier 150 is in electrical communication with connection points 138a and 138b using a pair of electrical connections 152a and 152b, respectively. Subcentimeter energy 154 is diagrammatically depicted as being incident on a lens 156 which serves to focus the subcentimeter energy onto antenna 136. In this regard, it should be appreciated that the sub-cm radiation need not be tightly focused onto the center of the antenna, but may incident on the detector body in a more general way. Lens 156 can be formed from any suitable material including, but not limited to sapphire, polytetrafluoroethylene or polyethylene. Detector laser energy 112 is focused into the central region of the interdigitated electrode structure, and causes a modulation of the conductance of the detector material at the offset frequency of the lasers 106 and 108. Detector laser energy 112 and subcentimeter energy 154 interact in the detector in a way which induces a signal across connection points 138a and 138b such that amplifier 150 outputs an electrical output signal 160 that is a downconverted version of the subcentimeter signal 154. If the offset between the frequencies of lasers 106 and 108 is arranged to be suitably close to the frequency of subcentimeter signal 154, the frequency of the electrical output signal 160 can be in a convenient range accessible by standard electronic laboratory equipment, such as 1 GHz or less. In this way, the properties of the subcentimeter signal 154 whose frequency will be typically beyond the reach of standard measurement techniques, can be studied by measuring downconverted signal 160 using standard available radio-frequency measurement equipment. The amplitude of the downconverted signal will be proportional to the intensity of the laser light 112 incident on the detector; to the extent that the detector can be designed to accommodate high power laser light without degradation, the sensitivity of the detection scheme may be correspondingly improved. It is noted that it may be helpful, for purposes of enhancing the reader's understanding of this highly advantageous technique, by considering "superheterodyne" radio receivers that are known in the art.

Having generally described the highly advantageous configuration of detector arrangement 100, it is appropriate to note that one having ordinary skill in the art will readily adapt this detection configuration to an application of interest in view of the detailed example below. In view of a particular application, factors such as, for example, incident power levels and noise levels should be considered in order to produce a downconverted electrical signal that is of interest. Applications for this detection arrangement and associated method are considered to include, but are not limited to communications systems, radio astronomy, spectroscopy (described below) and test and measurement instruments.

It is noted that the heterodyned lasers incident on the detector arrangement 100 have the effect of not only downconverting the sub-cm signal to a lower, intermediate frequency, but also of improving the sensitivity of the detection process. Also, it is further noted that the lasers illuminating the detector PCS need not necessarily be phase-locked to each other, or to the incident sub-cm radiation, in order to produce the desirable effects of downconversion of the incident sub-cm radiation to an intermediate frequency signal and improved detection sensitivity. Indeed, non-phase-locked lasers with a relatively less-precise frequency-tuning characteristic might still be useful for certain lower-resolution spectroscopy and detection applications, and would likely be more economical than other locking schemes discussed herein. The analysis of the downconverted signal amplitude presented below is equally applicable with respect to non-phase-locked lasers, without the phase cancellation effect to be described. While the detailed examples which follow are provided in terms of the use of subcentimeter radiation, it is to be understood that these examples are not intended as being limiting and that any implementation which applies the teachings that are brought to light herein, with respect to any suitable wavelength or frequency range, is considered to fall within the scope of the invention.

Attention is now directed to a discussion of the use of a detection arrangement, which shares the advantages of the detection arrangement of FIG. 1, in a specific system implementation. In particular, subcentimeter spectroscopy will now be described in detail, as practiced using a detection arrangement that is based on the aforedescribed arrangement of FIG. 1.

Figure 2:
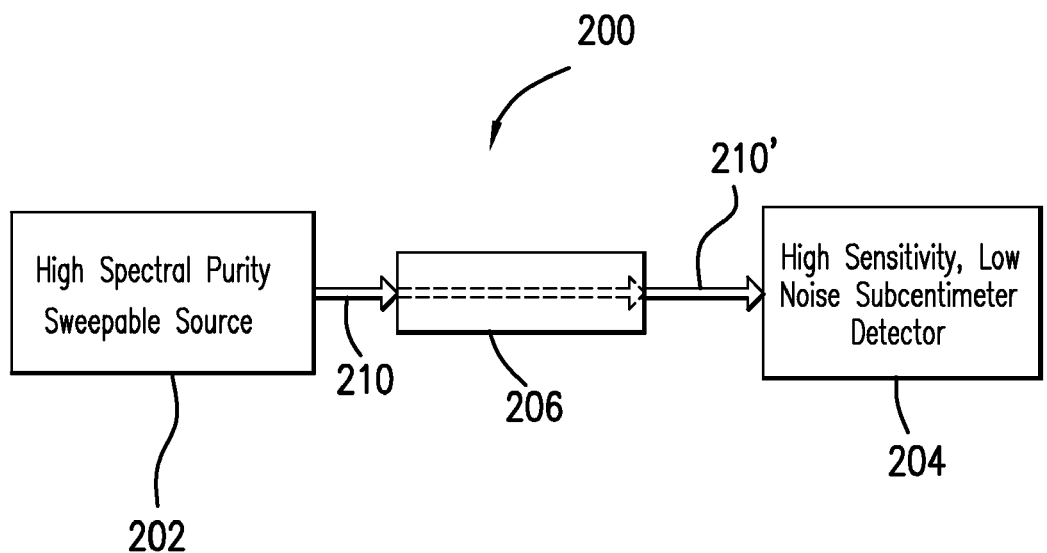
FIG. 2 is a block diagram which illustrates the configuration of a spectroscopy system including a detection arrangement that is based on the detection arrangement of FIG. 1.

Referring to FIG. 2, a spectrometer system configured for use in molecular spectroscopy is generally indicated by the reference number 200 and is illustrated in diagrammatic block diagram form. Spectrometer 200 includes a high spectral purity sweepable source 202 and a high sensitivity low noise subcentimeter detector 204. A sample region 206 is interposed between the source and detector such that subcentimeter radiation 210 emitted by source 202 passes through the sample region, thereby interacting with materials in the sample region to produce a sample influenced radiation 210'. In this regard, it is noted that molecular spectroscopy refers to the detection and characterization of molecular or bio-macromolecular gases present in the sample region [see references 2 and 3 below]. With high spectral purity source 202, that is capable of being swept in frequency, the rotational transitions in a molecular gas within the sample region can be measured, for example, at submm frequencies between 0.3 and 3 THz. The interaction of the molecular gas with the radiation characterizes the gas and makes the detection of specific molecules or bio-macromolecules possible.

Doppler limited transitions in molecular gases (i.e., in a low-pressure sample in which collisional broadening does not dominate) typically have a linewidth which is on the order of $1 \times 10^{-6}$ of the transition frequency. Therefore, a transition at 300 GHz would have a spectral linewidth of approximately 300 kHz and a transition at 1 THz would have a spectral linewidth of approximately 1 MHz. For purposes of spectroscopy, it would be desirable that the radiation produced by subcentimeter source 202 have a spectral purity of one-hundredth of the molecular transition linewidth and a spectral resolution which is on the order of one-thousandth of the molecular transition linewidth. While this may seem excessively stringent, in a field application it is extremely likely that there will be more than one molecular species in the sample and the high spectral purity will improve the ability to distinguish between spectroscopic lines of different molecules which may fall extremely close to one another. Since the transitions in bio-macromolecular samples are generally much, much broader than the Doppler limited transitions in a molecular gas, designing a spectrometer to meet the Doppler limited requirements will produce a system that can easily resolve bio-macromolecular gases.

Historically, submillimeter radiation (considered here as a class of subcentimeter radiation) has been produced with tube based devices like klystrons or Backward Wave Oscillators (BWOs). As solid state microwave components became available, these were also employed to achieve increasingly higher frequencies. There has even been a recent commercial announcement for a tunable THz gas laser (Coherent Technologies Inc). While these methods may be successfully implemented for laboratory based spectroscopy, it is noted that tube devices are bulky, solid state microwave devices that generally have a very narrow bandwidth and, with respect to the gas ion laser system, it is difficult to determine the operating frequency with high precision. It is thought that the present invention resolves all of these concerns by using optical mixing in a high mobility semiconductor, as will be described in detail below.

Figure 3:
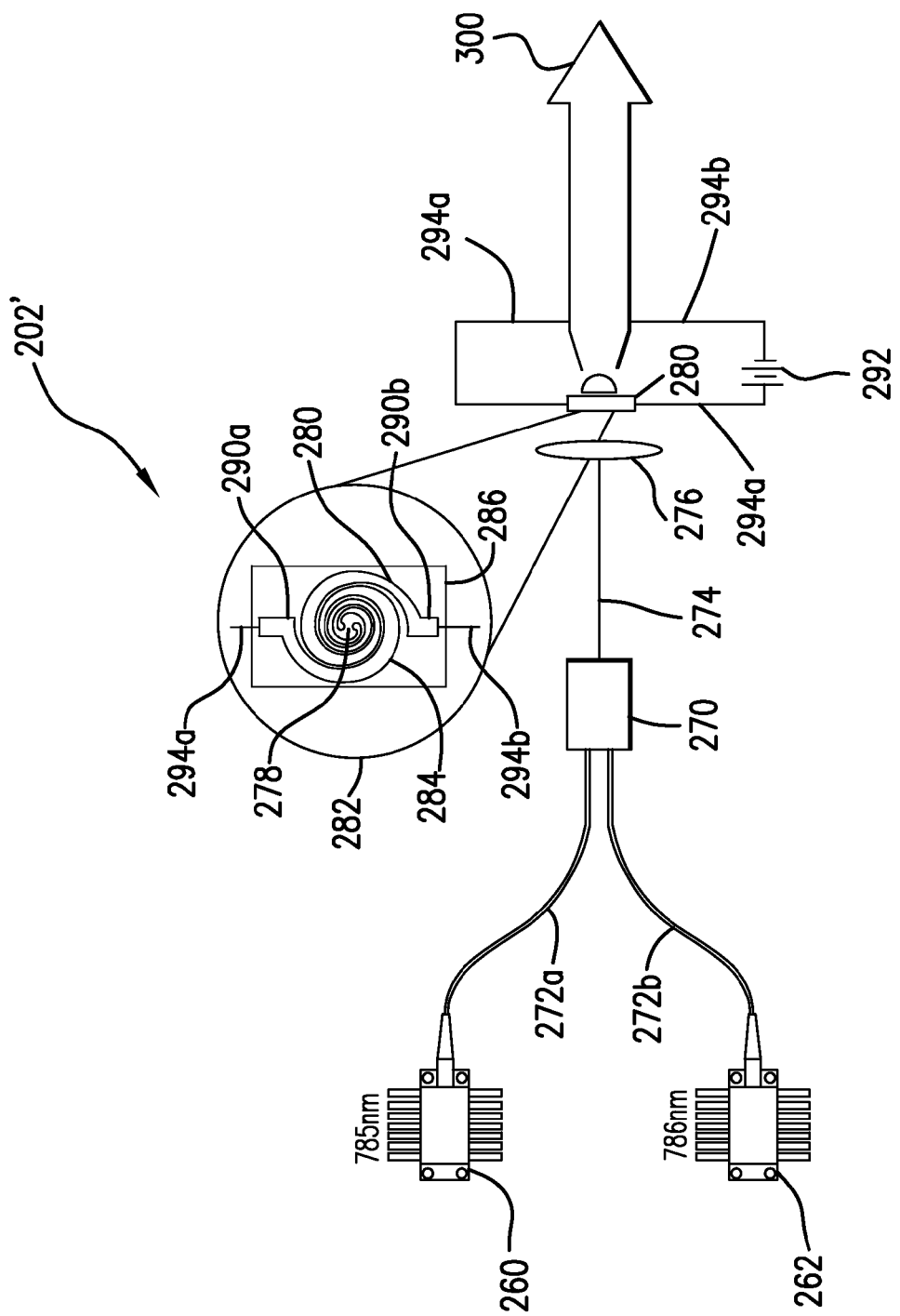
FIG. 3 is a diagrammatic plan view of one embodiment of a source arrangement that is useful in the system of FIG. 2.

Referring to FIG. 3, one embodiment of a source arrangement, that is suitable for use as part of system 200 of FIG. 2, is diagrammatically illustrated and generally indicated by the reference number 202'. It is to be understood that source 202' is not specifically required and that any suitable source arrangement can be used in system 200 so long as it produces an output that conforms with the various requirements set forth herein. Source 202' includes a first laser 260 and a second laser 262 connected using suitable optical conductors 272a and 272b, respectively, to an optical combiner 270 such that an output 274 from the optical combiner includes approximately equal contributions from each of lasers 260 and 262. It should be appreciated that the operational wavelengths of lasers 260 and 262 are established in terms of a desired difference frequency therebetween in the sub-cm range. Optical output 274 is incident on a lens 276 which may be formed from any suitable optical material. Lens 276 serves to focus the laser energy from output 274 onto a source PCS 280 that is additionally shown in an enlarged, plan view within a circle 282. In particular, lens 276 serves to focus the laser energy onto a small gap area 278 in the center of an antenna structure 284 that has been patterned onto an LTG GaAs body 286 of the photoconductive switch so as to define an opposing pair of connection points 290a and 290b that are electrically connected to a voltage bias source 292 using a pair of electrical leads 294a and 294b, respectively, thereby providing a DC electrical bias across antenna structure 284. The antenna pattern can be formed in any suitable manner such as, for example, by sputtering or MBE (Molecular Beam Epitaxy). Suitable materials include but are not limited to gold, gold/palladium or protected aluminum. Again, the antenna of Brown et al. [see reference 4 below] is useful. It is considered that one having ordinary skill in the art is capable of producing this antenna structure in view of the teachings of Brown et al. Using the exemplary laser wavelengths of 785 nm and 786 nm for lasers 260 and 262, biased antenna structure 284 radiates a subcentimeter difference frequency 300 of the two lasers, which, at this wavelength, is 480 GHz. It is noted that a range of laser wavelengths may be chosen, so long as this range is suitable for activating the photoconductive switch (generally, in the approximate range from 700 nm to 1100 nm). Also, it is noted that, although optical fiber interconnections are shown between lasers 260 and 262, optical coupler 270 and SPCS 280, any suitable arrangement of optical routing will also work, including free-space-optics using lenses and/or integrated optical waveguides. The lasers and coupler may also be monolithically integrated onto the same substrate.

Still referring to FIG. 3, while source 202' may produce subcentimeter radiation that is suited for coarse spectroscopy applications or for other applications, Applicants consider that simply mixing two free running lasers in a PCS will not generally produce sub-cm radiation with a linewidth which is suitable for molecular spectroscopy purposes with a desired accuracy. Therefore, in order to produce accurate mixing components, with a sufficiently narrow linewidth, it is generally appropriate to lock the two lasers to an optical frequency reference such as, for example, a Mode-Locked Laser (MLL), in a technique referred to as Photonic Synthesis, as will be further described below [see references 6 and 7 below]. This serves two functions: it establishes the sub-cm wavelength accuracy and the locking mechanism for the two lasers generally decreases the linewidth of the generated sub-cm radiation.

It is recognized that the concept of optical photo-mixing in semiconductor materials for the production of microwave and sub-mm radiation is not a new one. The bandwidth capability of such devices is generally limited by the lifetime of the optically produced charge carriers. When optical radiation in the wavelengths around 785 nm is incident upon LTG GaAs it produces electron-hole pairs with lifetimes on the order of 250 fsec and, therefore, radio-frequency signals can be generated with frequencies that can extend into the THz domain [see references 4, 7 and 8 below]. The LTG GaAs PCS generally has an inter-digitated, gold spiral antenna structure sputtered onto the surface [see reference 31 below]. This does two things: it allows a bias to be applied to the mixing area, and it dramatically improves coupling the sub-mm radiation into free-space. For typical devices, a bias of 25V to 50V is applied to the antenna structure and 50 mW of optical power is focused onto the inter-digitated section of the mixer. Such devices are capable of producing 100's of μW at 100 GHz and approximately 100 nW at 1 THz. This is an optical conversion efficiency of approximately 0.05% and 0.0002%, respectively. There is some indication that power at specific frequencies can be enhanced using a tuned antenna structure, but this will decrease the overall bandwidth of the PCS.

With respect to LTG source PCS 280. It is noted that most of the devices found in literature are produced by university research groups and are not commercially available. However, the LTG GaAs material is available from IQE Inc [see reference 5 below] and there are two options available for producing the Metal Semiconductor Metal (MSM) antenna structure: contract production with either a university or a semi-conductor fabrication company. Applicants are currently discussing limited production of the devices with Compound Semi-conductor of Scotland [see reference 6 below]. It is noted that future generations of these devices are contemplated having enhanced power generation. In particular, enhancements are desired with respect to improving the thermal sinking of the PCS, since the main failure mode of these devices is through ohmic or optical heating, and with respect to improving optical coupling into the semiconductor. Recently, a new material, ErAs/InGaAs, has come to light for sub-mm and THz production [see references 7 and 8 below]. The advantage of this material resides in the fact that ErAs absorbs at 1550 nm, as opposed to the 800 nm range, and therefore systems built at this wavelength can take advantage of all the devices currently developed for telecommunication applications.

Figure 4:
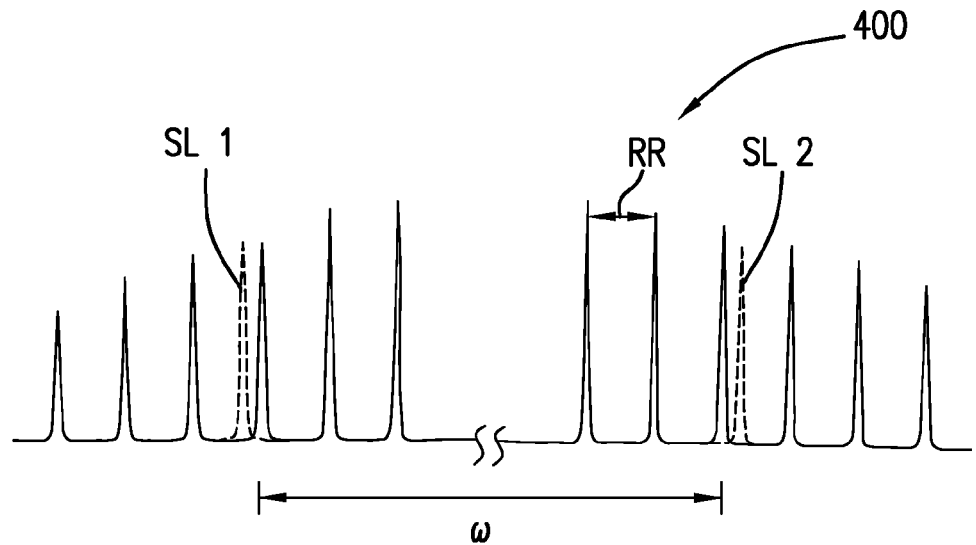
FIG. 4 is a plot of output amplitude versus frequency for a mode locked laser, shown here to illustrate a frequency comb that is produced by the laser and certain aspects of its use.
Figure 5:
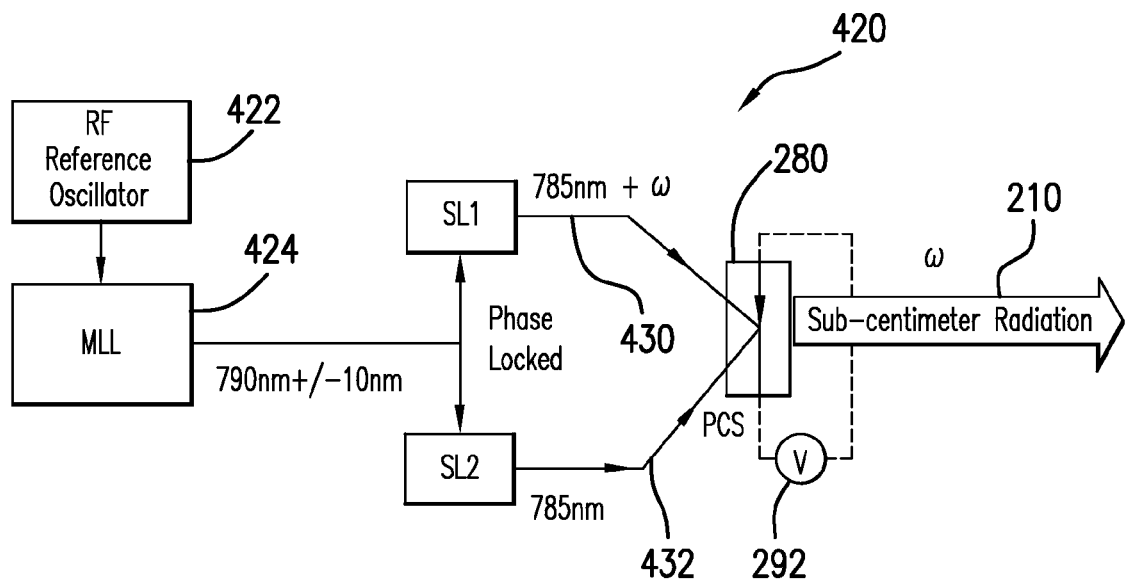
FIG. 5 is a block diagram of one embodiment of a source of subcentimeter energy which uses a mode locked laser.

Referring to FIGS. 4 and 5, the former illustrates a plot of output amplitude versus frequency, generally indicated by the reference number 400, for a mode locked laser. In Photonic Synthesis, an MLL serves as an 'optical local oscillator' or an optical frequency "comb" generator. One such frequency comb, in which the comb lines are formed by the individual frequency components of the MLL, is illustrated in FIG. 4. FIG. 5 illustrates an exemplary embodiment of a source of sub-centimeter energy, generally indicated by the reference number 420. In FIG. 5, the output from a highly accurate, spectrally clean microwave oscillator 422 is "up-converted" into the optical domain through the mode-locking process to become a series of optical modes with relative frequency stability determined by the frequency stability of the microwave oscillator. The resulting output from MLL 424 is the comb of wavelengths of FIG. 4, separated by the mode-lock frequency (or repetition rate, RR) equal to the output frequency of microwave oscillator 422, and spanning a bandwidth that is dependent upon the device, but may be as large as tens of nm (more than 4 THz at 785 nm). The output of mode locked laser 424 is coupled to a pair of slave lasers that are indicated as SL1 and SL2 such that the slave lasers are referenced or locked to individual comb lines (i.e., frequency components) of MLL 424. In the present example, SL1 and SL2 are distributed feedback (DFB) laser diodes (LDs). It is noted that other types of lasers could be utilized as one alternative to DFB LDs that have the required single-frequency operation and optical tuning range. Exemplary, non-limiting wavelengths are shown in FIG. 5 wherein slave laser 2 is operated at 785 nm while slave laser 1 is operated at 785 nm plus some offset ω. The optical outputs of the slave lasers are incident upon source PCS 280 so as to produce sub-centimeter output energy 210 at a difference or offset frequency Ω, between the locked operating frequencies of the two lasers. It is noted that the slave lasers may be independently locked to different optical frequency components of MLL 424. In this regard, the greater the bandwidth of the MLL, the larger the difference frequency, Ω, achievable between Slave Laser 1 (SL1) and Slave Laser 2 (SL2).

Still referring to FIGS. 4 and 5, locking refers to establishing a coupling or correlation between slave lasers SL1 and SL2 in which their phases are "locked," or varying synchronously. In order to meet Doppler limited spectroscopic requirements, it is considered to be advantageous to "lock" the slave lasers to MLL 424. In one implementation, this can be accomplished, for example, with an Offset Phase Lock Loop (OPLL). There are two major benefits of using an OPLL scheme as opposed to other possible schemes. First, an OPLL does not require that the wavelengths of the slave lasers match the output wavelengths of the MLL exactly. An offset frequency allows the slave laser to be "offset" from a mode of the MLL by any desired amount, as well as being locked to different, spaced apart modes or frequency components of the MLL. It is noted that the wavelengths of SL1 and SL2 are illustrated in the frequency spectrum of FIG. 4 as being offset from the frequency comb components of the mode locked laser. The second benefit resides in the fact that that the offset frequency may be swept. This will result in a corresponding frequency sweep in the resultant sub-cm radiation. In such an implementation, one or both laser outputs may be swept. For these reasons, it is suggested that a system employing an OPLL is highly advantageous as a source of sub-centimeter energy.

For purposes of measurement of the output of source 420, in the case of a MLL with 2 GHz mode spacing, the wavelength of the slave lasers is never greater than 1 GHz away from an optical frequency component of the MLL. This wavelength difference is easily measured by mixing the output from the MLL with the slave lasers on a photo-diode with a bandwidth greater than 1 GHz. While the absolute wavelength may not be known accurately, the difference frequency between SL1 and SL2 will be known as accurately as a 2 GHz signal may be measured.

Figure 6:
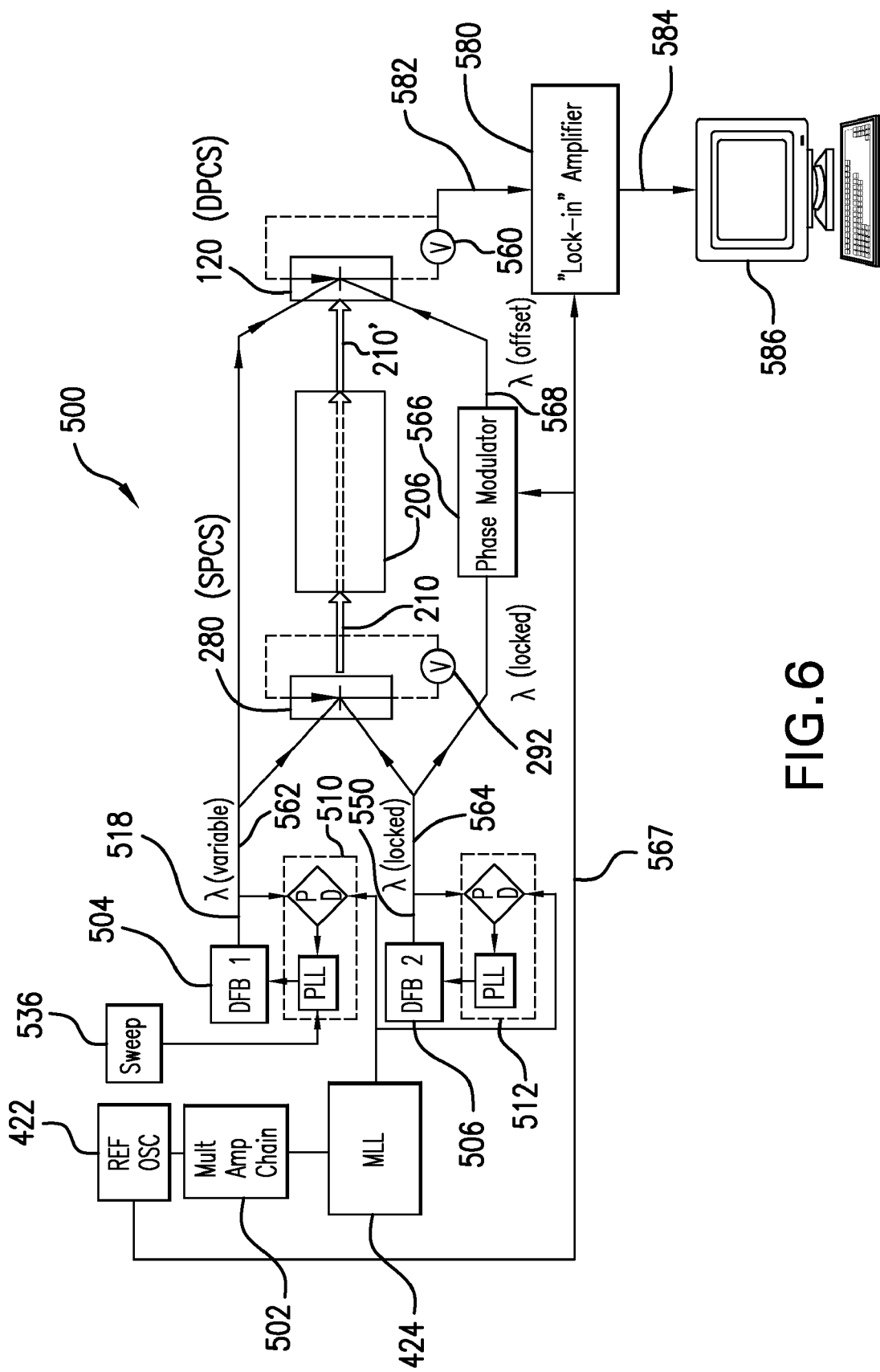
FIG. 6 is a block diagram of one embodiment of a spectroscopy system that is produced in accordance with the present invention.

Referring to FIG. 6, one embodiment of a complete spectroscopy system is illustrated, generally indicated by the reference number 500, in block diagram form. It is noted that optical paths are indicated by way of an enhanced line width, as compared to electrically conductive members, indicated by relatively narrow width lines. System 500 includes reference oscillator 422 coupled to MLL 424 via a multiplier amplifier chain 502 for electrical up-conversion of the RF reference oscillator from 125 MHz to approximately 2 GHz. The operation of mode locked lasers can be understood in the optical frequency domain as follows: in the absence of an electrical mode locking input signal, the MLL is an external cavity laser that will operate in multiple longitudinal cavity modes with random phases between them [see references 14 and 15 below]. When a strong modulation of the gain is applied from an external RF source, here at 2 GHz, each optical mode of the laser acquires sidebands due to the external modulation. When the frequency of the modulation signal equals the cavity mode spacing, the modulation sidebands mutually injection-lock the neighboring optical modes, causing all of the modes to establish a fixed phase relation between them. The result is a set of equally spaced cavity modes (at the repetition rate of 2 GHz, in the present example) that maintain a precise phase relationship to each other. As was alluded to previously, this is a useful technique for purposes of up-converting a highly-stable microwave signal to a series of highly-stable relative frequency offsets in the optical domain. It should be appreciated that MLLs are well understood and can be found in a wide range of alternative configurations. Moreover, MLL's make up but one of many available ways in which to produce phase correlated optical modes, any of which are considered as equally useful within the context of the present application. One alternative to the use of the MLL is the production of an optical comb through the deep phase modulation of a cw (continuous wave) laser using a resonant phase modulator as taught, for example, in reference [34]. At least for these reasons, specific design details with respect to the configuration of the MLL are considered to be beyond the scope of the present application.

Still referring to FIG. 6, system 500 uses a first DFB laser 504 and a second DFB laser 506 serving as first and second slave lasers, respectively. While the use of an Optical Phaselocked Loop (OPLL) is described herein, it should be appreciated that optical injection locking can alternatively be used to lock the slave DFB LDs to the MLL. The OPLL technique was selected for purposes of the present example. Accordingly, optical phase-locked loop control arrangements 510 and 512 are indicated within dashed lines for phase locking DFB 1 and DFB 2. Details with respect to OPLL will be provided immediately hereinafter.

Figure 7:
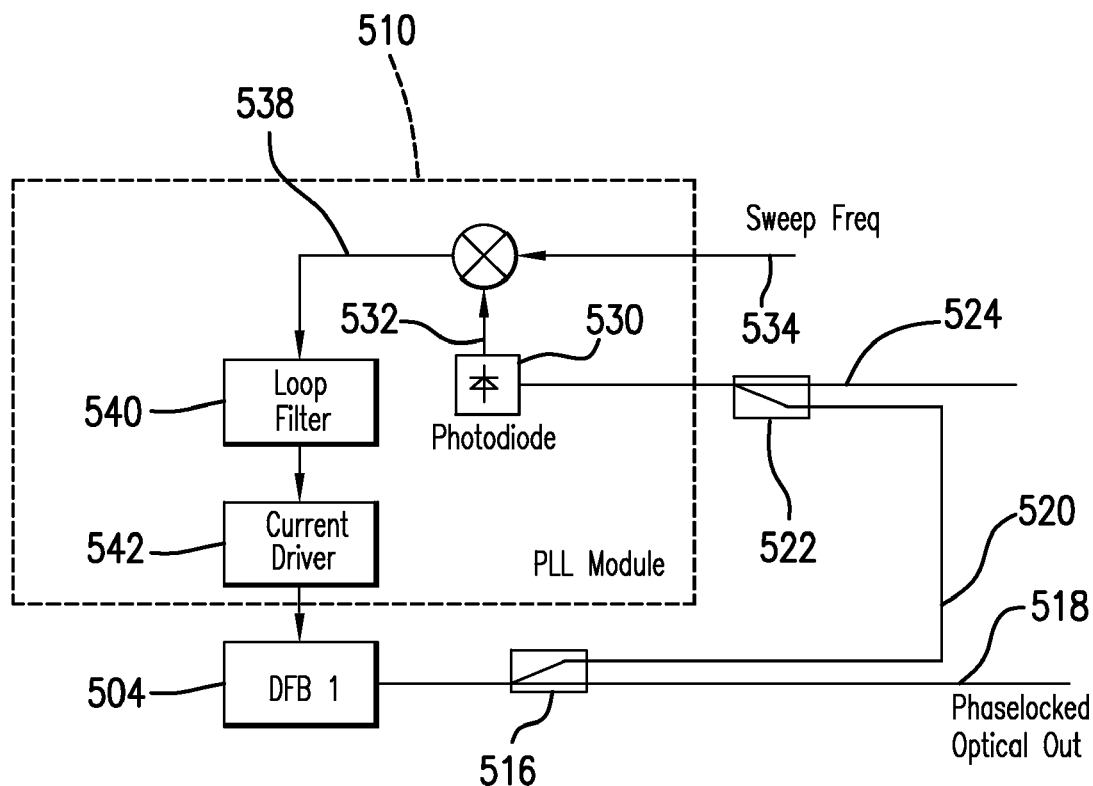
FIG. 7 is a more detailed block diagram of a portion of the system of FIG. 6, shown here to illustrate additional details with respect to phase locking a slave laser to a mode locked laser.

Turning to FIG. 7 in conjunction with FIG. 6, OPLL control arrangement 510 is illustrated in further detail, for use in controlling first DFB 510. In this configuration, the output of DFB 510 is coupled to a splitter 516, having one output 518 that comprises the phase-locked output laser light being produced. Another output 520 of splitter 516 is coupled to a combiner 522. The latter also receives the output of MLL 424 (FIG. 6) via an optical conductor 524. Initially, DFB 504 is tuned to within 0.9 GHz of a mode from the MLL. The signal from combiner 522 is detected using a high-speed photodiode 530 having at least a 2 GHz bandwidth. An output 532 of the photodiode is further mixed with an output 534 from a sweep frequency synthesizer 536 (FIG. 6) to produce a loop error output 538. The latter is then conditioned using a loop filter 540 and a current driver 542, prior to being provided to DFB 504. This control arrangement thus phase-locks the difference frequency between the slave laser and one of the MLL components to the frequency defined by the frequency sweep synthesizer. It should be appreciated that OPLL control arrangement 512 is essentially identical, except that a frequency sweep synthesizer is not required. In this regard, DFB 504 provides variable or swept output 518, while DFB 506 provides a locked or fixed output 550.

Referring to FIG. 6, system 500 further includes aforedescribed source PCS (SPCS) 280 for emitting sub-cm energy 210 which passes through sample or sample region 206 such that a portion thereof serves as sample influenced radiation 210' that is, in turn, incident upon detector PCS (DPCS) 120. DC bias is provided across the SPCS and the DPCS by DC voltage sources 292 and 560, respectively. A laser light conducting arrangement is provided including a first light path 562 from DFB 504 which illuminates SPCS 280 and DPCS 120 with the variable output from this laser. A second light path 564 is provided from DFB 506 which illuminates SPCS 280 with the locked output and further provides the locked laser energy to a phase modulator 566, forming part of the second light path and which uses the frequency output of reference oscillator 422, provided on a line 567, to phase modulate the optical energy on the second light path to produce a phase modulated output 568 from the locked laser output of DFB 506 to a concluding portion of the second light path which illuminates DPCS 120 with the phase modulated output of modulator 566. The laser illumination of DPCS 120, from the first and second light paths, mixes with sub-cm sample influenced radiation 210' in a way which produces a mixing component in the form of an electrical output signal across the body of the DPCS (see connection points 138a and 138b of FIG. 3). This downconverted electrical signal is directly related to and influenced by sample influenced energy 210' such that characteristics of the sample that are induced in the sample influenced energy are also present in the electrical output signal. Accordingly, a lock-in amplifier 580, or functionally equivalent electronic receiving circuit, is connected to the DPCS by a line 582 and is used for purposes of detecting the electrical output signal and providing it on an output 584 thereof. An analysis system 586 converts the electrical output signal to digital form and produces a direct measurement of discrete absorptions versus the sub-cm frequency due to the sample that is in the optical path of the sub-cm radiation.

Every molecule has particular absorption characteristics which leads to the ability to "fingerprint" individual molecules in a sample. This fingerprint can then be compared, for example, to reference fingerprints that are saved within an overall library in analysis system 586. It is considered that one having ordinary skill in the art is capable of appropriately programming analysis system 586 in view of this overall disclosure. Additional descriptions with respect to the operational details of operation of system 500 will be provided below.

One potential problem with sweeping DFB 504 occurs when the desired offset frequency is near or equal to one-half of the MLL comb spacing (1 GHz in the present example). Under such a condition, the photo-detector output will contain two frequency components near one-half the comb spacing and this will cause an ambiguity for the locking circuit. This is easily remedied, however, by altering the offset of the second DFB LD (which is normally locked to a single wavelength) by some defined amount and then offsetting the sweeping DFB LD by this same amount to maintain the same difference frequency. This allows the first DFB LD to "skip" the ambiguous region of the locking range. Once that region is cleared for the first DFB LD, the second DFB LD is reset to its normal offset. Since the frequency sweep of the sub-cm radiation is actually a series of frequency steps by the variable or swept slave laser, this process is invisible to the spectrometer.

It is noted that the Atacama Large Millimeter Array (ALMA) radiotelescope project describes using heterodyne mixing of two DFB LDs that are referenced to an optical frequency comb to produce low noise sub-mm radiation to frequencies of 950 GHz [see reference 20]. While there are a number of references with respect to DFB LDs that are phase-locked to other DFB LDs, only the ALMA project appears to explicitly describe a reasonably related photosynthesis technique. This reference indicates that the noise floor at 100 kHz from a 150 GHz carrier is −75 dBc/Hz. For a Lorentzian line-shape, this implies a linewidth of approximately 2 kHz at 150 GHz, or two parts in $10^8$. For Doppler limited molecular spectroscopy, this is more than adequate. However, there are many trade-offs in designing an OPLL system and the final sub-cm linewidth will depend significantly at least on the locking bandwidth, the offset tuning range and offset tuning rate. It may be necessary to choose a linewidth that is wider than achievable to allow the sub-cm radiation to be swept at a satisfactory speed, particularly with respect to the development of future systems.

Having described the photonic synthesis configuration of system 500 above, it is appropriate to note that Distributed Feed-Back Laser Diodes incorporate an etched grating in the waveguide section of the device which narrows the linewidth and provides wavelength selection through temperature or current tuning. The temperature responsivity of a typical DFB LD is 0.1 nm/C. This implies a tuning range of approximately 7 nm (−20 C to 50 C). Since the source PCS in the photonic synthesizer mixes the output from two DFB LDs, the effective tuning range is doubled, or approximately 14 nm, and will result in a tunable difference frequency of at least 6.8 THz at 785 nm (480 GHz/nm). This is more than adequate for the applications that are contemplated herein. The linewidth, however, is set by the length of the grating structure in the waveguide and, for a free-running DFB, is typically 0.1-10 MHz. It is important to understand, as will be further described, that one aspect of the source resides in the fact that, once the slave DFB LDs are properly locked to the frequency comb from the MLL, the phase fluctuations between the slave DFB LDs are correlated [see references 6 and 7]. Therefore, when these optical signals are mixed in the source PCS, the resulting linewidth of the sub-cm radiation is much narrower than that achievable with two free-running DFB LDs.

While optical phase-locked DFB LDs are considered to be useful in the context of the present invention, there is at least one alternative method that can be employed that trades circuit complexity for laser complexity: external cavity lasers. These lasers are similar in construction to the MLL; a semiconductor gain element is in a cavity with a grating which is employed for wavelength selection. Such schemes are commonly reported in the literature as having linewidths on the order of 100-300 Hz [see reference 24]. Unlike the DFB LDs it is not necessary to phase lock the external cavity lasers to decrease the relative linewidth because their linewidth is already extremely narrow. Simply mixing the output of the external cavity slave laser with the output from the MLL on a photodiode ("frequency locking") would produce a beat frequency which could be employed for measuring the difference frequency of the two slave lasers. A frequency sweep would simply be accomplished by quickly scanning the wavelength of one of the external cavity devices and using the optical modes of the MLL as markers, similar to the method employed with the submm FASST System where an external microwave cavity is used for frequency reference [see reference 25].

Three important characteristics of a spectrometer are frequency accuracy, spectral purity and bandwidth (frequency scanning ability). Spectral purity and bandwidth were addressed above, but a discussion with respect to frequency accuracy is merited at this juncture. Fortunately, one of the key points of photonic synthesis resides in the fact that each optical output component of the MLL is an exact harmonic of the drive oscillator, which itself is dependent upon the reference oscillator, which can be a highly accurate oven-controlled crystal oscillator. Since the sub-cm radiation is generated by beating two optical signals against each other (which are themselves locked to a mode of the MLL) the absolute optical frequency does not need to be known and the difference frequency is directly correlated to the output from the oven-controlled electronic oscillator.

Initially, it is necessary to calibrate the wavelength of the DFB LDs to their respective currents and temperatures so that for a given temperature and current, it is possible to calculate which harmonic of the MLL they are locked to. Given this information and, in the case of an OPLL system, knowing the offset frequency, the limit to the frequency accuracy is dependent upon the oven controlled crystal oscillator. A Vectron CO-725SA19-L2 Oven Controlled Oscillator (OCXO) operating at 125 MHz has a frequency drift of $2 \times 10^{-9}$ per day [see reference 26]. While this amount seems small, it will scale with harmonic which implies that at 1 THz there exists a frequency drift of 2 kHz/day. There are currently techniques for using a GPS (Global Positioning System) receiver to establish a frequency traceability to the National Institute of Standards and Technology (NIST) to an uncertainty of better than $1 \times 10^{-12}$ when averaged over a day [see reference 27]. So, with the condition that the system has access to the GPS system, frequency accuracy should be better than 2 kHz at 1 THz.

Another method that could be employed to routinely calibrate the system of FIG. 6, whereby to maintain accuracy, would be to measure the "fingerprint" of a molecular standard, such as Carbonyl Sulfide (OCS). As a simple linear molecule with a transition spacing of 12 GHz and an absorption peak around 500 GHz, OCS is a good standard. Further, as a molecular standard it is available in small, easily portable cylinders.

One linewidth broadening mechanism that will occur is due to un-correlated phase noise in the MLL which degrades the optical up-conversion process. This phase noise is dependent upon the square of the difference in harmonic number between the two modes employed for locking [see reference 28]. For a 2 GHz repetition frequency this means that the difference in mode number necessary to produce a 1 THz mixing product is 500. Given that commercially-available quartz ovenized oscillators that could be employed for this spectrometer can be obtained with phase noise of −145 dB/Hz at 1 kHz offset from a 100 MHz carrier (for example, a Vectron model CO-724S [see reference 26]), the noise of a 2 GHz signal generated by multiplication of this oscillator will be increased by a factor of 20×, or 26 dB, to approximately −119 dBc/Hz. The noise on actively mode locked semiconductor lasers follows the noise characteristics of the reference oscillator fairly accurately [see reference 25] (i.e., assume within 20 dB), so the noise limit at 1 THz will be approximately 500×, or 54 dB higher, to yield −65 dBc/Hz at 1 KHz offset from a 1 THz signal. Because these phase fluctuations will be correlated between the SPCS and the DPCS, they will not have an impact on the sensitivity of the detector (as will be shown below), but at increasing harmonic differences, such phase fluctuations will increasingly degrade the spectral purity. It is noted that if a reference oscillator is used that has lower phase noise, correspondingly lower phase noise at THz frequencies is to be expected.

Referring to FIGS. 5 and 6, coarse frequency control and sweeping of the sub-cm radiation can be achieved by simply locking the two slave lasers to harmonics of the MLL that have the desired difference frequency. Changing the harmonics to which SL1 and SL2 are phase locked can be employed to "step" through a frequency range in 2 GHz intervals. In such a configuration, the frequency accuracy of the sub-cm radiation will depend upon reference oven controlled oscillator 422, frequency multiplier chain 502, and any added noise of MLL 424, as discussed previously. Continuous sweeping of the sub-cm radiation in fractions of the 2 GHz MLL mode spacing is also possible. This can be accomplished in a two step process: first, the offset of the OPLL is swept with low power voltage controlled sweep oscillator 536 to the extent of its range, and then a different mode of the MLL is chosen and the sweep is performed again. The greater the frequency range of the voltage controlled oscillator, the greater the range that can be swept before it becomes necessary for the OPLL to employ a different mode of the MLL for locking, but this stepping and sweeping process should be invisible to the spectrometer. Accurate frequency reference can be achieved by mixing the output from voltage controlled sweep oscillator 536 with reference oscillator 422.

Referring to FIG. 6, in view of the foregoing, attention is now directed to a discussion with respect to the detection configuration that is employed in system 500. Although FIG. 6 illustrates an OPLL system, it is important to understand that the following mathematical derivation is independent of the method that is used to lock the DFBs to their respective wavelengths.

Considering the specific implementation of FIG. 6, the output from wavelength locked DFB 506 is phase modulated by optical phase modulator 566 before it is mixed with the output from wavelength variable DFB 504 on DPCS 120. As will be illustrated in the mathematical derivation, this will result in a phase modulation term that is only present when sub-cm radiation 210' falls onto DPCS 120. Employing a phase sensitive detection scheme (i.e. lock-in amplifier 580 or functional equivalent), measurement of the sub-cm mixing on the DPCS at the modulation frequency is enabled with extremely narrow bandwidth and, therefore, high noise rejection [see reference 30]. In this configuration, the output from reference oscillator 422 drives not only MLL 424, but is also used to drive phase modulator 566 and to trigger lock-in amplifier 580. This configuration still further improves common-mode noise rejection.

To understand the signal amplitudes and detector noise in system 500, it is first necessary to describe the LTG GaAs PCS behavior in heterodyne mixing [see reference 31]. While portions of the following descriptions are couched in terms of THz, it is to be understood that the discussion is equally applicable with respect to subcentimeter energy. The photo-conductance of the PCS is effectively modulated by the intensity variation of the input optical source at the difference frequency between the two lasers. When two single-mode lasers of power levels $P_1$ and $P_2$ and frequency $v_1$ and $v_2$ are incident on a biased PCS, the instantaneous optical power, $P_i(t)$, may written:

$$P_i(t) = P_1 + P_2 + 2\sqrt{mP_1P_2}[\cos(2\pi(v_2-v_1)t + \cos(2\pi(v_2+v_1)t] \quad (1)$$

Where m is the mixing efficiency with value between 0 and 1 depending on the spatial overlap and polarization alignment of the two beams. It is assumed that the photo-conductance only responds to the difference frequency between the two beams, which is in the sub-cm-wave band, and not at the frequency of the second term, which is at twice the optical frequency. Accordingly, the second term is dropped in the analysis that follows. The relationship of the conductivity of LTG-GaAs with the mixing of the two optical signals has been treated previously [see reference 31] and shows that the expression for the modulated photo-conductance, G(t), of the PCS due to the heterodyne laser input may be written as:

$$G(t) = \frac{\eta_i T \tau e N_g^2 (\mu_e + \mu_h) P_o}{hv(N_e w_e + N_g w_g)} \left(1 + \frac{2\sqrt{mP_1P_2}\sin(\omega t + \phi)}{P_o\sqrt{1+\omega^2\tau^2}}\right) \quad (2)$$

$$G_0 = \frac{\eta_i T \tau e N_g^2 (\mu_e + \mu_h) P_o}{hv(N_e w_e + N_g w_g)} \text{ and } \beta = \frac{2\sqrt{mP_1P_2}}{P_o\sqrt{1+\omega^2\tau^2}} \quad (3)$$

$$\equiv G_0[1 + \beta\sin(\omega t + \phi)] \quad (4)$$

Where $\eta_1$ is the internal quantum efficiency (number of photocarrier pairs that are generated per photon entering the photomixer material), $\omega$ is $2\pi f$, $w_g$ is the width of the gap between electrodes, $w_e$ is the width of the electrodes, hv is the photon energy, $N_e$ is the number of illuminated electrodes, $N_g$ is the number of gaps, $\mu_e$ and $\mu_h$ are the electron and hole mobilities, respectively, $\tau$ is the top air to GaAs interface power transmissivity, $\phi = \tan^{-1}(1/\omega\tau)$, $P_0 = P_1 + P_2$ or the total incident power averaged over a long time period, T. It is noted that these terms are defined as they appear in reference [31]. For simplicity of notation, the following convention for denoting the various radian frequencies and phases that arise have been adopted in the analysis as follows (where n and m are dummy indices):

$$\omega_{n-m} = 2\pi(v_n - v_m) \quad (5)$$

$$\omega_{n+m} = 2\pi(v_n + v_m) \quad (6)$$

$$\phi_{n-m} = \phi_n(t) - \phi_m(t) \quad (7)$$

Hereinafter, terms with subscript L refer to the frequency and the phase of the light from the locked DFB laser, for example, $v_L$ and $\phi_L$ and terms with subscript M refer to the locked laser light after passing through the phase modulator. Subscript V refers to the variable laser. The heterodyne signal incident on the source PCS results in photo-conductance modulation at frequency $\omega_{V-L}$. The light incident on the detector PCS results in photo-conductance with a frequency of $\omega_{V-M}$ and a phase modulation at frequency f. The time-dependent conductance G(t) modulates the bias current at frequency $\omega_{n-m}$, thus delivering power to the load at this frequency. The resulting current is given by:

$$I(t) = V_{bias} G(t) \quad (8)$$

Where $V_{bias}$ is the bias voltage that is applied by source 292 in FIG. 6. In the SPCS, this photo-induced current couples to the antenna and generates free-space sub-cm radiation that is focused into the sample cell, and then received by the antenna on the DPCS. The conversion efficiencies from incident heterodyne optical power to radiated sub-cm power for various inter-digitated electrode structures on LT-GaAs are reported in reference [31]. In general, the efficiency remains flat at low frequencies up to a corner frequency determined by the carrier lifetime and device capacitance, where it then drops at approximately 12 dB/Octave.

The THz power received at the DPCS is reduced by the detector conversion efficiency and the frequency-dependent absorption of the sample under test. The THz power is expressed in the detection PCS as:

$$P_{THz-D} = \alpha(\omega) G_{ant} P_{THz-S} \quad (9)$$

where $\alpha(\omega)$ is the frequency-dependent absorption characteristic of the sample under test, $G_{ant}$ is a term that incorporates all coupling losses, including those due to the collimation optics as well as the antenna coupling efficiency and the conversion efficiency recently addressed for the SPCS and $P_{THZ-S}$ represents the power emitted by the source. The actual radiated THz power from the SPCS, as well as its coupling into the DPCS antenna, may also depend on other factors such as antenna geometry, polarization, antenna gain and other parasitic losses.

The THz power incident on the DPCS generates a THz sinusoidally-varying voltage $V_{THz}(t)$ across the inter-digitated electrode structure that adds to the externally-applied DC bias voltage in the DPCS. It is assumed that the rms value of this THz voltage is related to the received THz power simply via the base conductance $G_o$ of the DPCS ($G_{o,D}$), so that:

$$V_{THz}(t) = \sqrt{\frac{2P_{THZ-D}}{G_o}} \cos(\omega_{V-L}t + \phi_{V-L}(t)) = \quad (10)$$

$$V_{THZo}\cos(\omega_{V-L}t + \phi_{V-L}(t))$$

The THz radiation received by the DPCS antenna adds to the DC bias. Also, the DPCS has an incident optical heterodyne signal at $\omega_{V-M}$ This results in an induced current in the DPCS of:

$$I_D(t) = G_{0,D}[V_{bias} + V_{THz}(t)][1 + \beta\sin(\omega_{V-M}t + \phi_{V-M}(t))] \quad (11)$$

Substituting the full expression for the THz voltage into equation (11) yields:

$$I_D(t) = G_{0,D}[V_{bias} + V_{THZo}\cos(\omega_{V-L}t + \phi)][1 + \beta\sin(\omega_{V-M}t + \phi_{V-M}(t))] \quad (12)$$

Expanding and re-arranging this the full expression for the current in the DPCS is obtained:

$$I_D(t) = G_{0,D}V_b + G_{0,D}V_b\beta_D \sin(\omega_{V-M}t + \phi_{V-M}(t)) + G_{0,D}V_{THzo}\cos(\omega_{V-L}t + \phi_{V-L}(t)) + G_{0,D}\beta_D V_{THzo} \cos(\omega_{V-L}t + \phi_{V-L}(t))\sin(\omega_{V-M}t + \phi_{V-M}(t)) \quad (13)$$

The first term in equation (13) is a DC current. The second and third terms represent time-varying currents in the THz frequency range and the last term represents a down-converted IF (Intermediate Frequency) signal. The interest here resides in ultimately calculating the signal amplitude and noise of the IF signal, from which the projected sensitivity of the proposed spectrometer system can be understood. Therefore, the last term of the previous equation becomes the focus of attention. Expanding the last term of equation (13), and rewriting it:

$$I(t) = \qquad (14)$$
$$G_{0,D}V_b + G_{0,D}V_b\beta_D\sin(\omega_{V-M}t + \phi_{V-M}(t)) +$$
$$G_{0,D}V_{THzo}\cos(\omega_{V-L}t + \phi_{V-L}(t)) + \frac{G_{0,D}\beta_D V_{THzo}}{2}$$
$$(\sin((\omega_{V-M} + \omega_{V-L})t + \phi_{V-M}(t) + \phi_{V-L}(t)) +$$
$$\sin((\omega_{V-M} - \omega_{V-L})t + \phi_{V-M}(t) - \phi_{V-L}(t)))$$

Where, $$\omega_{V-M} = 2\pi(\nu_V - \nu_L) = \omega_{V-L} \qquad (15)$$

$$\phi_{V-M}(t) = \phi_V(t) - (\phi_L(t) + A\cos(2\pi f_m t)) \qquad (16)$$

A is the modulation depth and f is the modulation frequency. Making these substitutions and dropping all the terms at other frequencies other than the modulation frequency results in the following current:

$$I_{Df}(t) = \frac{G_{0,D}\beta_D V_{THzo}}{2}\sin(A\cos(2\pi f_m t)) \qquad (17)$$

This is considered as a remarkable result. Specifically, the common-mode phase-noise terms cancel and the only term remaining is that due to the phase modulation. That is, as a result of the correlation of the laser energy that is incident on the SPCS and the DPCS, the first order common-mode phase noise cancels. Moreover, this result obtains in any implementation disclosed herein in which the laser energy is correlated, irrespective of the laser locking technique or the specific form of modulation that is applied by that particular implementation.

While the lowering of the noise floor is desirable, the actual measurement resolution will depend on the absolute linewidth of the THz signal that propagates through the sample cell, and will depend on the degree of phase correlation between the lasers incident on the SPCS. Also, to realize the common-mode cancellation of the laser phase noise, there are practical issues to be considered in the construction of the system, such as the need to match the path lengths closely to prevent discrimination of the phase fluctuations. However, packaging techniques can render this a tractable problem.

Another interesting result from equation (17) is that when the THz power is zero, the current at f (the phase modulation frequency) will be zero: no frequency modulated signal can be detected without the presence of the radiation from the SPCS. This is simply due to the fact that there will be no downconverted intermediate frequency signal generated without the presence of the radiation from the SPCS.

Figure 8:
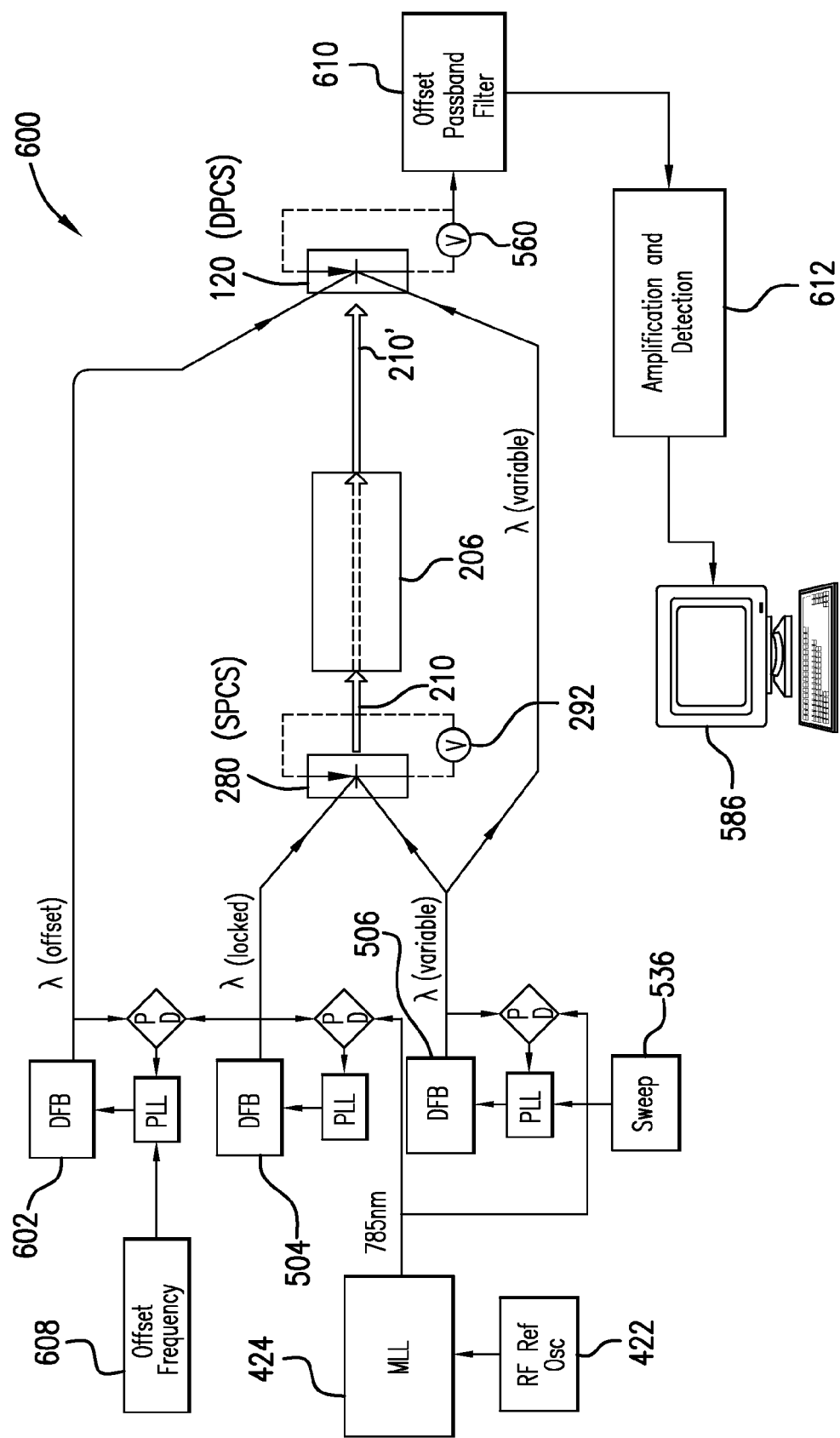
FIG. 8 is a block diagram of another embodiment of a spectroscopy system that is produced in accordance with the present invention.

FIG. 8 is a first alternative embodiment of a spectroscopy system, produced in accordance with the present invention and generally indicated by the reference number 600. In this embodiment, three DFB lasers 602, 504 and 506 are referenced to MLL 424 which, in turn, is referenced to highly stable RF oscillator 422. An OPLL arrangement is used with each of the lasers, as described above. Hence, descriptions of the phase locked loop components will not be repeated for purposes of brevity. The wavelengths of the λ(locked) DFB 504 and λ(variable) DFB 506 are chosen so that the heterodyne output from source PCS 280 is the sub-cm wavelength of interest. The λ(variable) DFB 506 is then swept in wavelength, using sweep generator 536, which results in sweeping the sub-cm radiation. For detection, the output from λ(locked) DFB 504 is used to lock third DFB 602 at an offset frequency that is produced by an offset frequency generator 608. The output of λ(offset) DFB 602 is then mixed with λ(variable) 506 laser energy on Detection PCS. A resulting downconverted electrical IF output signal at the offset frequency is passed through a lock-in or narrow-band filter 610 set at the offset frequency and into an amplifier 612 which produces an amplified electrical output signal for use by analysis system 586. It is noted that amplifier 612 is optional, based on a particular implementation. If sub-cm radiation 210' from Source PCS 280 is not present on Detection PCS 120, then the mixing of the λ(offset) and λ(variable) optical signals at the DPCS will not result in production of the IF component, but in the frequency difference of the two optical signals. Hence, there will be no electrical output signal. If, however, radiation 210' from the Source PCS is incident on the Detection PCS, the mixing will produce the IF component at the offset frequency which then passes through the filter and is amplified. This is commonly referred to as super-heterodyne down conversion.

Another interesting point about the super-heterodyne detection scheme is that it can be used to measure not only the amplitude of the sub-cm signal transmitted through the sample (i.e., absorption spectroscopy), but also the resultant phase versus frequency. Operation of the spectrometer in this mode would be analogous to that of a vector network analyzer. It makes the spectrometer capable of measuring the phase, group delay and refractive index of the material being analyzed versus frequency. This additional information could potentially enhance the detection of spectral signatures of threats versus false alarms. As is the case with all spectroscopy embodiments described herein, use of the MLL as the local oscillator causes phase noise, which is present on each of the MLL components, to be highly correlated and, therefore, this phase noise cancels out in the first order mixing products at the DPCS.

Figure 9:
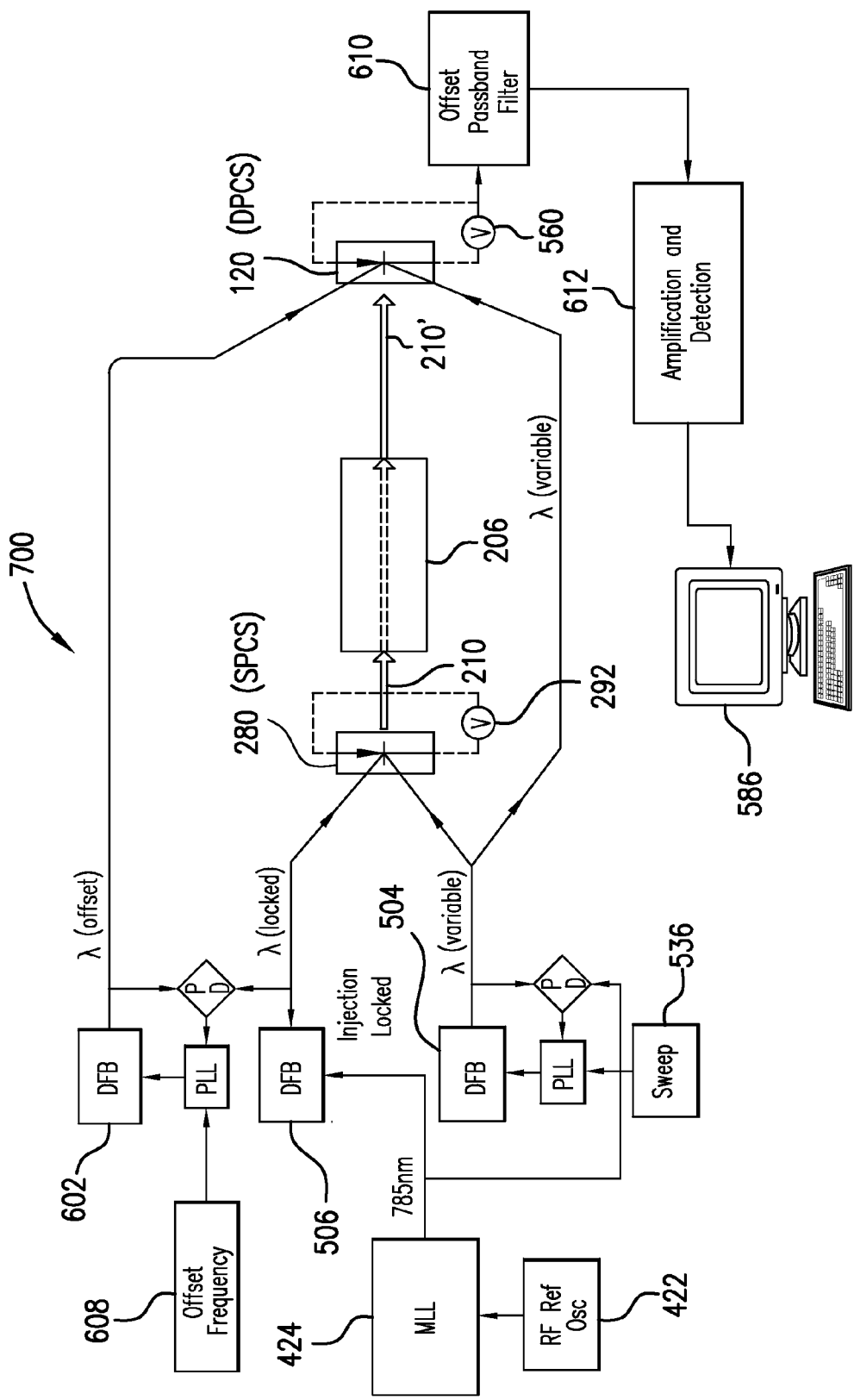
FIG. 9 is a block diagram of still another embodiment of a spectroscopy system that is produced in accordance with the present invention.

In the event that higher spectral purity is required and it is not possible to obtain sufficiently narrow linewidth DFBs, there are options employing DFB lasers. For example, a hybrid system is illustrated in FIG. 9, indicated by the reference number 700 and which shares the basic configuration and components of system 600 of FIG. 8. In particular, only λ(locked) DFB laser 504 is optically injection locked. Injection locking only λ(locked) DFB 504 is advantageous since it improves spectral purity with the additional advantage that the system no longer requires a third OPLL circuit. Scanning and offsetting can still be performed by OPLL DFBs 506 and 602, respectively. This provision can decrease the linewidth of the sub-cm radiation. The only potential drawback is the characteristic difficulty in maintaining optical injection locking. However, it is noted that if a solution to this difficulty is forthcoming, the attractiveness of the optical injection-locked approach increases.

Figure 10:
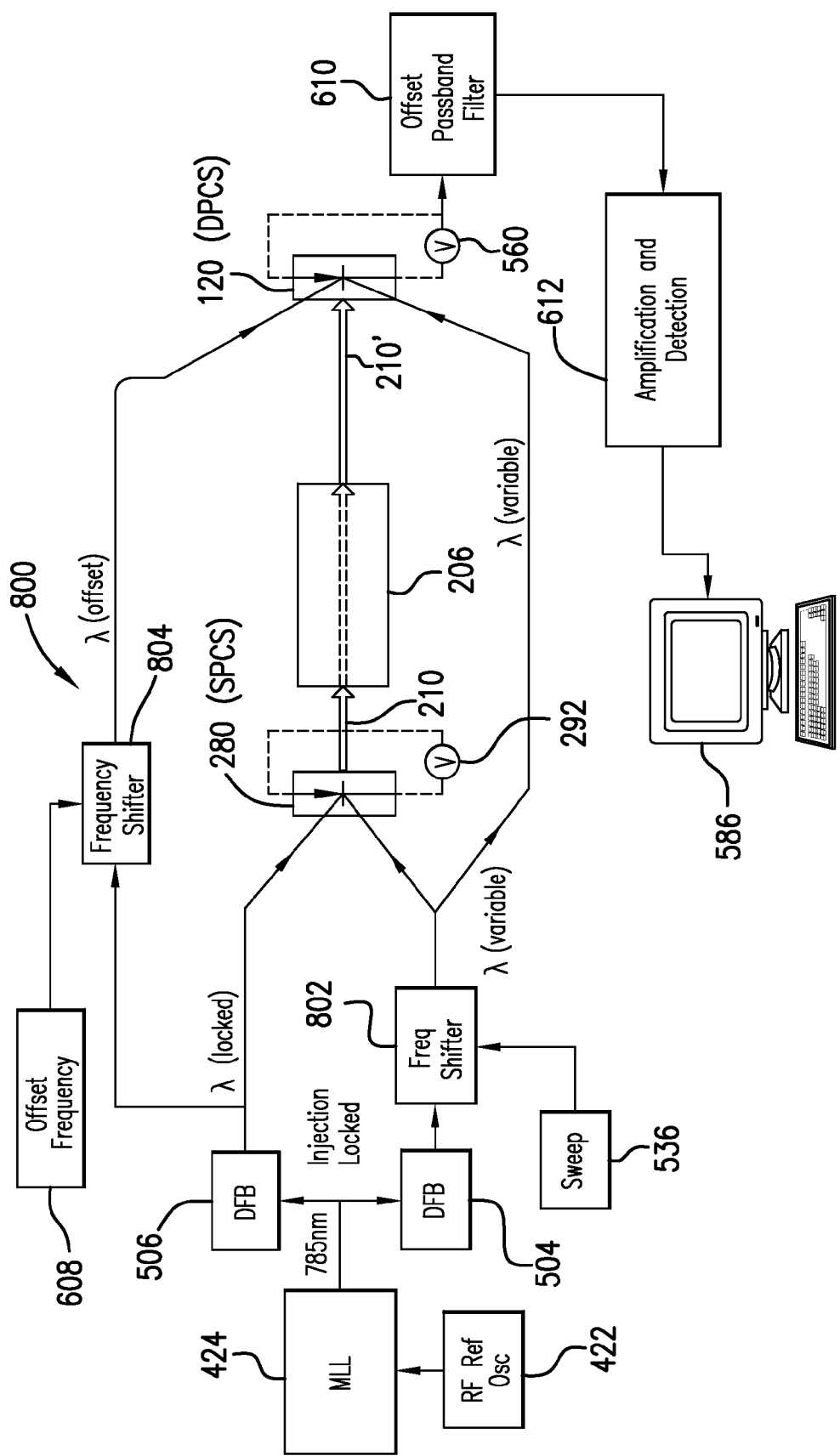
FIG. 10 is a block diagram of yet another embodiment of a spectroscopy system that is produced in accordance with the present invention.

Turning to FIG. 10, a fully injection locked system is generally indicated by the reference number 800 and serves as another example of an option with respect to the use of DFB lasers where sufficiently narrow linewidths are not available. It is noted, however that a fully injection locked system is considerably more difficult to implement, since the addition of a first frequency shifter 802, for producing the λ(variable) light, and a second frequency shifter 804, for producing the λ(locked) light are required in order to scan and offset, respectively. Further, the injection lock on two DFB lasers must be maintained. However, all of the common-mode phase noise cancellation properties of the scheme, discussed previously, still obtain.

Figure 11:
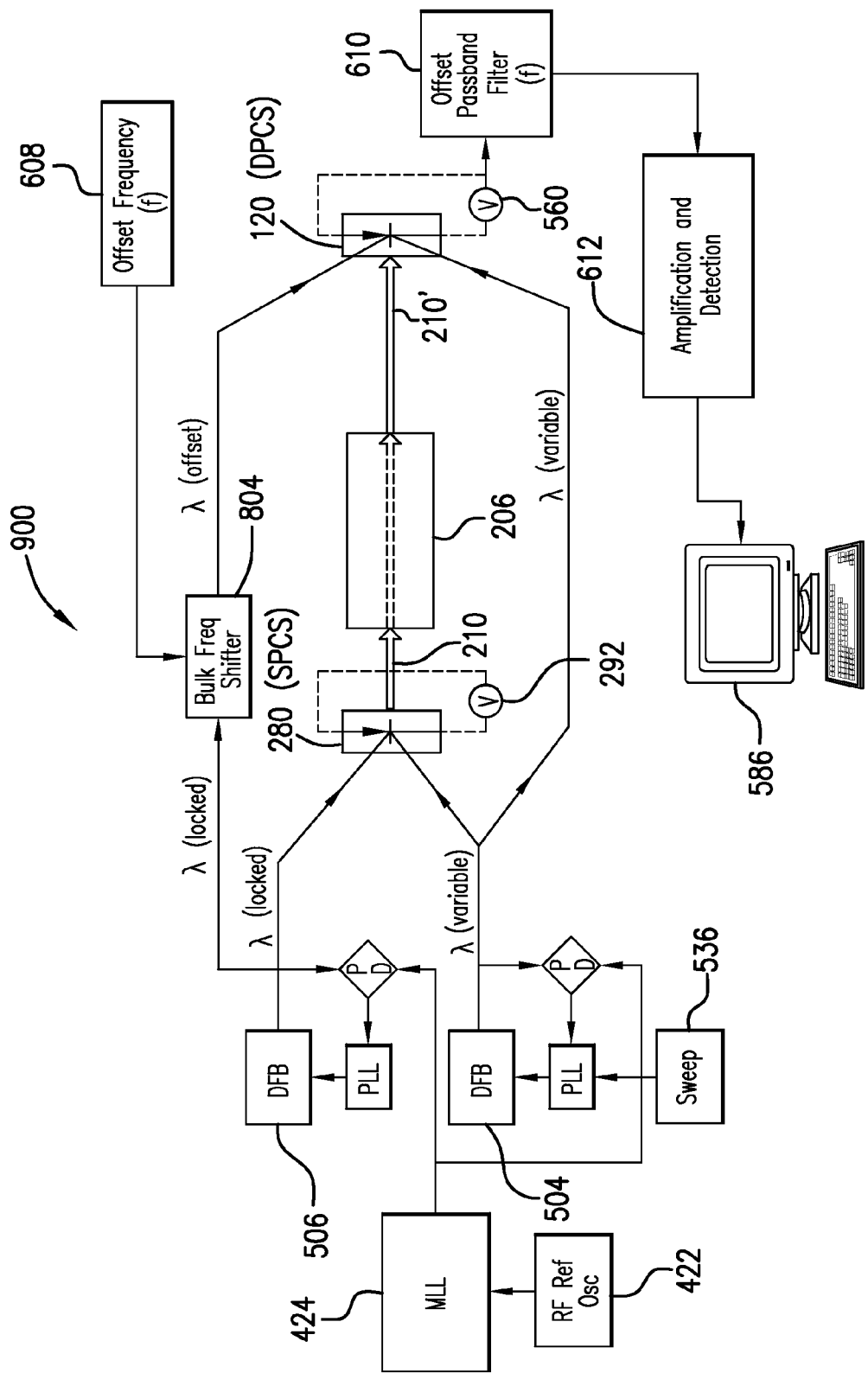
FIG. 11 is a block diagram of an additional embodiment of a spectroscopy system that is produced in accordance with the present invention.

Attention is now directed to FIG. 11 which illustrates another alternative implementation of a spectroscopy system, generally indicated by the reference number 900. This system represents a phase locked version of the injection locked system of FIG. 10.

In view of the alternative system configurations that have been brought to light herein, it is noted that the frequency offset or phase offset required for the highly advantageous detection scheme disclosed herein can be implemented or achieved in many different ways. Accordingly, these examples are intended as being exemplary and nonlimiting. For example, other alternative configurations may utilize optical frequency shifters or dual phase modulators (one on each of the slave laser optical conductors in advance of the DPCS).

Figure 12:
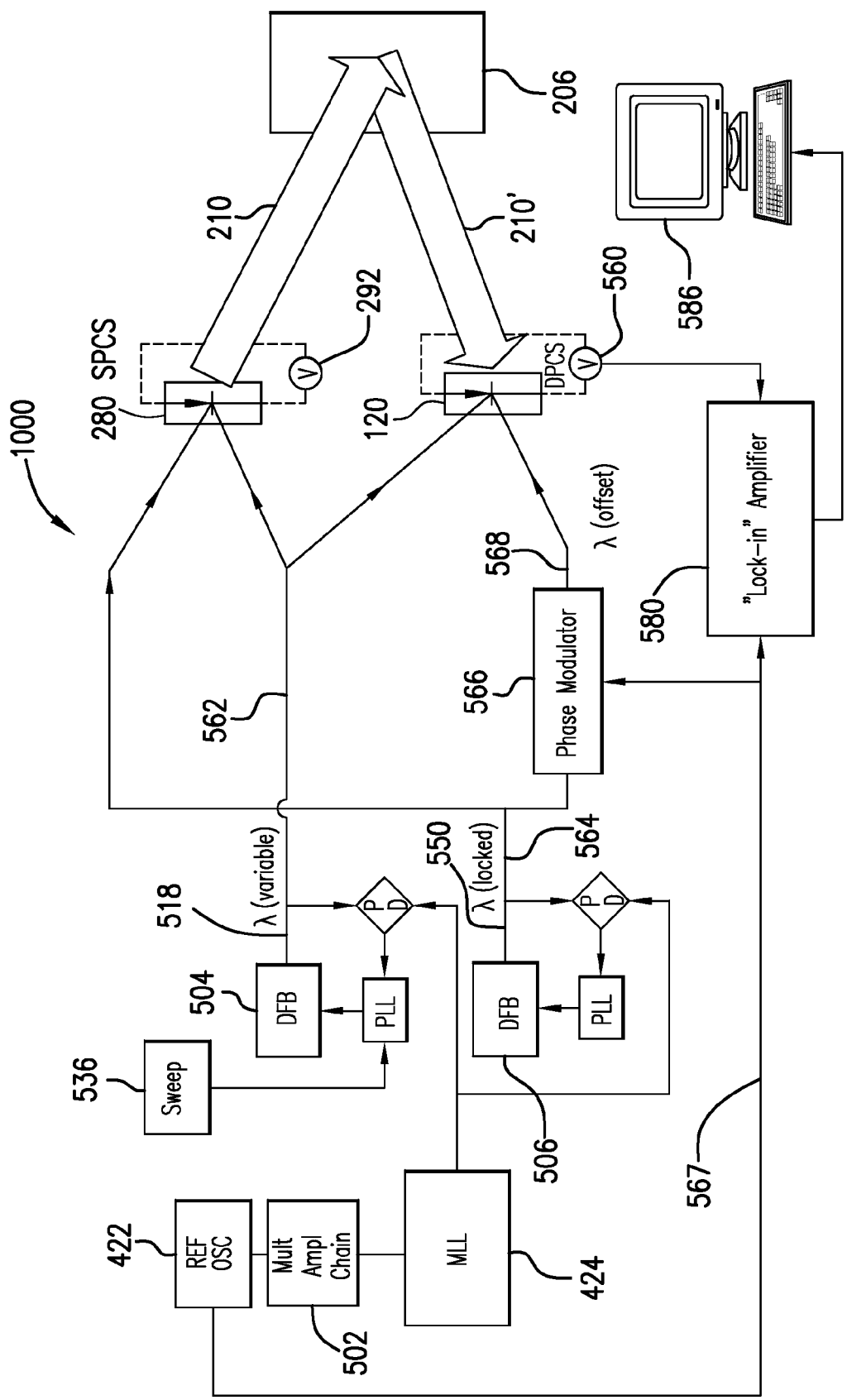
FIG. 12 is a block diagram of one embodiment of a spectroscopy system that is produced in accordance with the present invention and which uses a reflection measurement scheme.

Turning to FIG. 12, another embodiment of a spectroscopy system is generally indicated by the reference number 1000. From the standpoint of the various components that are used, this system is essentially identical to system 500 of FIG. 6. Unlike system 500, which relates to measurement of sample absorbance in a transmission type setup, system 1000, the same absorption measurements can be achieved in a reflective measurement as illustrated in FIG. 12 by the arrangement of subcentimeter radiation 210 and sample influenced radiation 210'.

Figure 13:
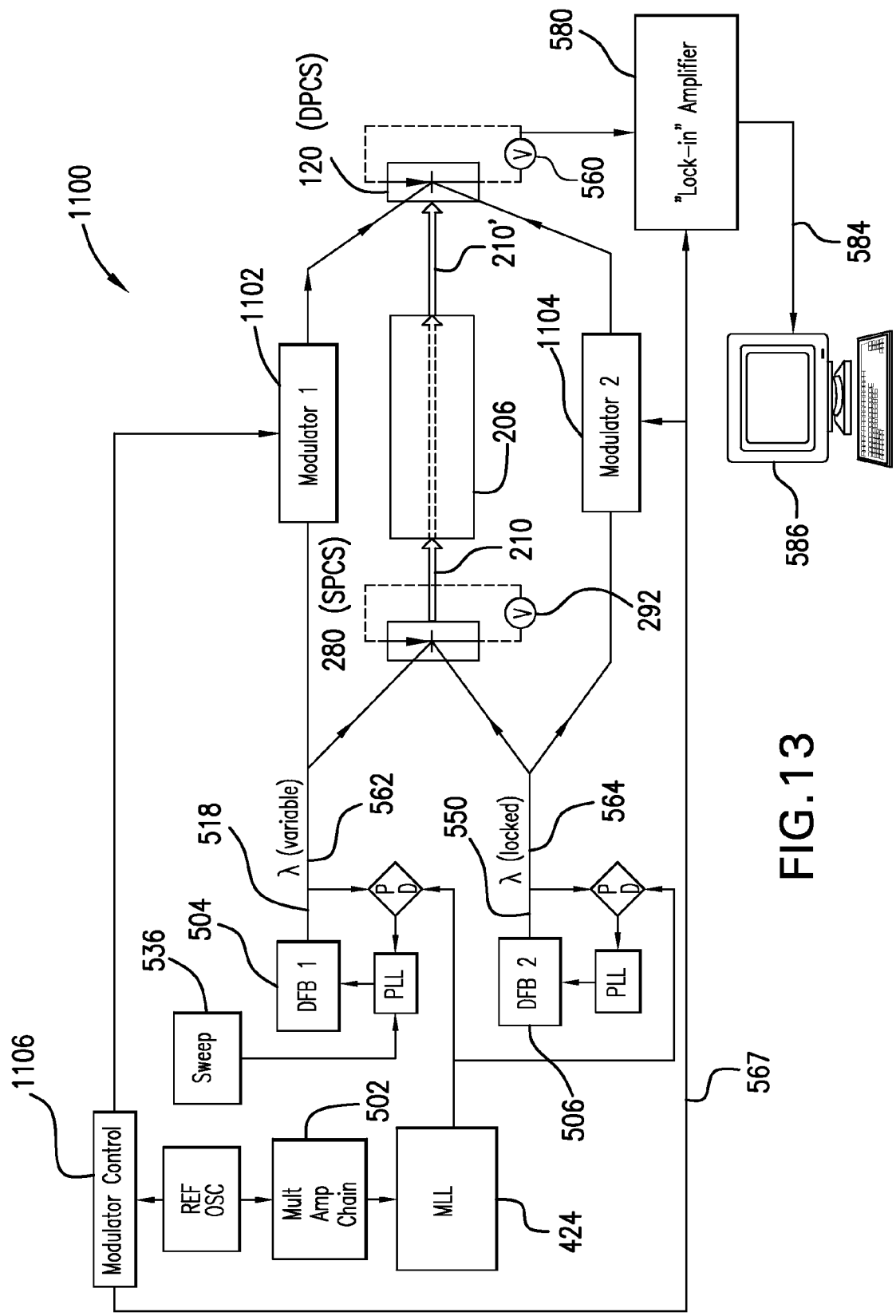
FIG. 13 is a block diagram of a further embodiment of a spectroscopy system that is produced in accordance with the present invention using a differential modulation scheme.

Referring now to FIG. 13, a further embodiment of a spectroscopy system is generally indicated by the reference number 1100. This system, like system 1000 of FIG. 12, uses many like components and includes an overall configuration that resembles that of system 500 of FIG. 6 with a few exceptions to which the present discussions will be limited. In particular, system 1100 includes a pair of modulators 1102 and 1104 for purposes of implementing differential modulation of the overall laser light that is used to illuminate detector PCS 120. Modulators 1102 and 1104 are controlled by a modulator controller 1106 that provides drive signals to both modulators to produce the desired differential phase (or frequency) modulation of the lasers. It is noted that any suitable form of modulation can be used for differential modulation purposes such as, for example, phase modulation and frequency modulation. The use of differential modulation can produce a higher modulation depth for a given type of optical modulator and drive signal, which can at least potentially improve the system sensitivity compared to a single modulator.

LIST OF REFERENCES

Using the descriptions above, in conjunction with the various figures, it is considered that one of ordinary skill in the art may readily practice the present invention in view of the teachings therein. However, for further explanatory purposes, the following references may be cited at one or more points in the description. Certain ones of these references include technical content and are hereby incorporated by reference. Other references are provided, for example, with respect to manufacturers or potential producers of components that are relevant at various points in the discussions.

1. Peter H. Siegel, *Terahertz Technology* IEEE Transactions on Microwave Theory and Techniques, 2002 50(3): p 910-28. See, in particular pages 915 to 917 and the references within.
2. C. H. Townes and A. L. Schawlow, *Microwave Spectroscopy*. 1955, New York: McGraw-Hill Book Company, Inc.
3. P. F. Bernath, *Spectra of Atoms and Molecules*. 1995, New York: Oxford University Press.
4. E. R. Brown, K. A. McIntosh, K. B. Nichols, and C. L. Dennis. *Photomixing up to 3.8 THz in low-temperature-grown GaAs*. Appl. Phys. Lett. 1995. 66(3): p. 285-7.
5. K. A. McIntosh, E. R. Brown, K. B. Nichols, O. B. MaMahon, W. F. DiNatale, and T. M. Lyszczarz. *Terahertz photomixing with diode lasers in low-temperature-grown GaAs*. Appl. Phys. Lett. 1995. 67(26): p. 3844-6.
6. AFRL-SN-RS-TR-1999-268 *Radio Frequency Photonic Synthesizer* Rome Research Site DARPA D965.
7. See Chapter 10 on "Photonic Link Techniques for Microwave Frequency Conversion" pp. 293-327, by S. A. Pappert, R. Helkey, and R. T. Logan Jr., in *RF Photonic Technology in Optical Fiber Links*, W. S. C. Chang, Ed., Cambridge University Press, 2002.
8. S. Verghese, K. A. McIntosh, and E. R. Brown *Optical and terahertz power limits in the low-temperature-grown GaAs photomixers*. Appl. Phys. Lett. 1997. 71(19): p. 3743-5.
9. K. A. McIntosh, E. R. Brown, K. B. Nichols, O. B. MaMahon, and W. F. DiNatale. *Terahertz measurements of resonant planer antennas coupled to low-temperature-grown GaAs photomixers*. Appl. Phys. Lett. 1996. 69(24): p. 3632-4.
10. IQE Inc North America Manufacturing Plant. 119 Technology Drive. Bethlehem, Pa., 18015 Tel: (1) 610-861-6930 (http://www.iqep.com)
11. Compound Semiconductor Technologies Global Ltd. Block 7, Kelvin Campus West of Scotland Science Park. Maryhill Road. Glasgow G20 OTH. Scotland, UK. Tel.: +44(0)141-579-3000
12. M. Sukhotin, E. R. Brown, D. Driscoll, M. Hanson, and A. C. Gossard. *Picosecond photocarrier-lifetime in ErAs:InGaAs at 1.55 µm*. Appl. Phys. Lett. 2003. 83(19): p. 3921-23.
13. M. Sukhotin, E. R. Brown, A. C. Gossard, D. Driscoll, M. Hanson, P. Maker, and R. Muller. *Photomixing and photoconductor measurements in ErAs:InGaAs at 1.55 µm*. Appl. Phys. Lett. 2003. 82(18): p. 3116-8.
14. A. E. Siegman, "Lasers." 1986, Sausalito: University Science Books.
15. A. Yariv, "Optical Electronics." $2^{nd}$ ed 1985, New York: Holt, Rinehart and Winston.
16. M. P. Kesler, and E. P. Ippen, Femtosecond Time-Domain Measurements of Group Velocity Dispersion in AlGaAs Diode Lasers. Electron. Lett. 1989. 25(10): p. 640-2.
17. Ramaswamy-Paye, M and J. G. Fujimoto, *Compact dispersion-compensating geometry for Kerr-lens mode-locked femtosecond lasers*. Opt. Lett. 1994. 19(21): p. 1756-8.

18. J. R. Demers, and F. C. De Lucia, *Modulating and Scanning the Mode-lock Frequency of a 800 MHz Femtosecond Ti:sapphire Laser*. Opt. Lett. 1999. 24(4): p. 250-2.
19. InPhenix 250 North Mines Rd. Livermore, Calif. 94551 Tel: 925 606 8809
20. S. Pengbo, P. A. Davies, W. P. Shillue, L. R. D'Addario and J. M. Payne. *Millimeter Wave Generation Using an Optical Comb Generator with Optical Phase-Locked Loops*. ALMA memp #439. 2002-10-31.
21. Sacher Lasertechnik, LLC. 5765 Equador Way, Buena Park, Calif. 90620 Tel: (714) 670-7605
22. Koheras A/S, Blokken 84, DK-3460 Birkerød, Denmark +45 4348 3900
23. A. Schoof, J. Grunert, S. Ritter, and A. Hemmerich, *Reducing the linewidth of a diode laser below 30 Hz by stabilization to a reference cavity with finesse above $10^5$*. Opt. Lett. 2001, 26(20): p. 1562-4.
24. D. T. Petkie, T. M. Goyette, R. P. A. Bettens, S. P. Belov, S. Albert, P. Helminger and F. C. DeLucia. *A Fast Scan Submillimeter Spectroscopic Technique*, Rev. Sci. Instrum., vol. 68 no. 4 pp. 1675-1683, pr. 1997.
25. Vectron, 1-800-328-7661
26. National Institute of Standards and Technology. *Using a Global Positioning System (GPS) receiver as a NIST traceable frequency reference*.
27. D. von der Linde, *Characterization of the noise in Continuously Operating Mode-Locked Lasers*. Appl. Phys. B, 1986. 39: p 201-217.
28. D. J. Erickson, P. A. Morton, J. E. Bowers and R. L. Thornton, Comparison of timing jitter in external and monolithic cavity mode-locked semiconductor lasers, Appl. Phys. Lett. 59 (26) 23 Dec. 1991 pp. 3372-4.
29. Stanford Research Systems Technical Note#3 "About Lock-In Amplifiers." 1290-D Reamwood Avenue Sunnyvale, Calif. 94089
30. E. R. Brown, F. W. Smith and K. A. McIntosh. *Coherent millimeter-wave generation by heterodyne conversion in low-temperature-grown GaAs photoconductors*. J. Appl. Phys. 1993. 73(3): p. 1480-84.
31. Miteq, 100 Davids Drive, Hauppauge, N.Y. 11788 (613) 436-7400
32. Mini-Circuits World Headquarters P.O. Box 350166, Brooklyn, N.Y. 11235 U.S.A. (718) 934-4500
33. S. M. Iftiquar, Kiyomi Sakai, Masahiko Tani, Bambang Widiyatmoko, Motonobu Kourogi, Motoichi Otsu, "Attempt to Generate Narrow Linewidth, CW Terahertz Radiation by Using Optical Frequency Comb." 8-th International Conference on Terahertz Electronics, Sep. 28-29, 2000 in Darmstadt, Germany, pp. 221-223

Although each of the aforedescribed physical embodiments have been illustrated with various components in particular respective arrangements, it should be understood that the present invention may take on a variety of specific configurations with the various components being located in a wide variety of alternative configurations. Furthermore, the methods described herein may be modified in an unlimited number of ways, for example, by reordering, modifying and recombining the various steps. Accordingly, it should be apparent that the arrangements and associated methods disclosed herein may be provided in a variety of different configurations and modified in an unlimited number of different ways, and that the present invention may be embodied in many other specific forms without departing from the spirit or scope of the invention. Therefore, the present examples and methods are to be considered as illustrative and not restrictive, and the invention is not to be limited to the details given herein.

What is claimed is:

1. A system for investigation of a sample, said system comprising:
    a source arrangement having a source frequency response;
        a detector arrangement in a positional relationship with said source arrangement such that said sample is located in relation to the source arrangement and the detector arrangement, and said detector arrangement having a detector frequency response; and
    a laser illumination arrangement for generating
        (i) a source laser energy that is produced by at least two lasers that are offset phase locked with respect to one another and which source laser energy is incident on said source arrangement, based on the source frequency response, in a way which causes the source arrangement to emit subcentimeter radiation, at least a portion of which subcentimeter radiation interacts with said sample and the source laser energy interacts to produce a frequency sweep in the subcentimeter radiation and, thereafter, at least some of said portion of the subcentimeter radiation serves as a sample influenced radiation that is incident on the detector arrangement, based on said positional relationship, and
        (ii) a detector laser energy that is incident on said detector arrangement and offset phase locked with the source laser energy in a way which produces at least one optical component of the detector laser energy that is offset with respect to a corresponding optical component of the source laser energy so that the detector laser energy and the sample influenced radiation interact, based on said detector frequency response, in a way which at least generates an electrical output signal across the detector arrangement such that the electrical output signal is responsive to the sample influenced radiation including said frequency sweep.

2. The system of claim 1 wherein said optical component of the detector laser energy is offset by a phase shift with respect to the corresponding optical component of the source laser energy.

3. The system of claim 1 wherein said optical component of the detector laser energy is offset by a frequency shift with respect to the corresponding optical component of the source laser energy.

4. The system of claim 1 including an arrangement for recovering said electrical output signal.

5. The system of claim 4 including a processing arrangement for using said electrical output signal in a way which serves to identify said sample.

6. The system of claim 5 wherein said processing arrangement is configured for responding to at least one of a phase shift and an amplitude change that is present in said electrical output signal and induced responsive to said subcentimeter radiation passing through said sample.

7. The system of claim 1 wherein said source arrangement is a photoconductive switch.

8. The system of claim 7 wherein said source arrangement includes a source body formed using LTG ErAs/GaAs.

9. The system of claim 1 wherein said detector arrangement is a photoconductive switch.

10. The system of claim 9 wherein said detector arrangement includes a detector body of the detector photoconductive switch that is formed using LTG ErAs/GaAs.

11. The system of claim 1 wherein said source laser energy and said detector laser energy are each characterized by a phase fluctuation characteristic and said illumination arrangement is configured for correlating the phase fluctuation characteristic between the source laser energy and the detector laser energy to cause the detector laser energy to cooperate with the subcentimeter radiation in a way which produces a modified phase fluctuation characteristic of said electrical output signal that is less than the phase fluctuation characteristic of the source laser energy and the detector laser energy.

12. The system of claim 1 wherein said laser illumination arrangement produces said source laser energy as a first laser energy having a first wavelength that is incident on said source arrangement and having said frequency sweep and a second laser energy having a second wavelength, different from said first wavelength, that is also incident on said source arrangement so that the source arrangement mixes the first laser energy and the second laser energy to produce said subcentimeter radiation with said frequency sweep, and said laser illumination arrangement produces said detector laser energy in a first light path that is configured for using said first laser energy with said frequency sweep to illuminate the detector arrangement with a first light path laser energy and in a second light path that is configured for using said second laser energy to illuminate the detector arrangement with a second light path laser energy such that at least one of the first light path laser energy and the second light path laser energy is offset with respect to a respective one of the first laser energy and the second laser energy to cause mixing of the (i) first light path laser energy, (ii) the second light path laser energy and (iii) the subcentimeter radiation at the detector arrangement to produce at least said electrical output signal responsive to the subcentimeter radiation and said frequency sweep, as influenced by said sample.

13. The system of claim 12 wherein said first light path includes a first light path modulator for using the first laser energy to produce said first light path laser energy.

14. The system of claim 13 wherein said first light path modulator is a phase modulator.

15. The system of claim 13 wherein said second light path includes a second light path modulator for using the second laser energy to produce said second light path laser energy.

16. The system of claim 15 wherein said first light path modulator and said second light path modulator cooperate to form an overall differential modulator.

17. The system of claim 16 wherein said overall differential modulator is configured to use a selected one of phase modulation and frequency modulation.

18. The system of claim 12 wherein said electrical output signal is produced only when said subcentimeter radiation is incident on the detector arrangement along with the detector laser energy.

19. The system of claim 12 wherein said laser illumination arrangement includes a mode locked laser for producing an output frequency comb and said laser illumination arrangement further includes a first laser and a second laser for producing a first laser energy and a second laser energy, respectively, and for producing a modified laser energy using the third laser energy, and a phase locking arrangement for offset phase locking the first laser, the second laser, the third laser energy and, thereby, the modified laser energy to the frequency comb such that a phase fluctuation characteristic is correlated between the first laser energy, the second laser energy and the modified laser energy and said laser illumination arrangement is configured for using said modified laser energy, which also includes said phase fluctuation characteristic, correlated with the phase fluctuation characteristic of the first and second lasers to produce the detector laser energy as a combination of the modified laser energy and the second laser energy, and said detector arrangement uses said detector laser energy and said subcentimeter radiation in a way which produces a modified phase fluctuation characteristic, in said electrical output signal that is less than the correlated phase fluctuation characteristic of the first laser energy, second laser energy and third laser energy.

20. The system of claim 19 wherein said detector arrangement uses the second laser energy, modified laser energy and subcentimeter radiation such that the phase fluctuation characteristic, correlated therebetween, cancels at least to a limited extent in producing the modified phase fluctuation characteristic.

21. The system of claim 19 wherein said first, second and third lasers are semiconductor laser diodes.

22. The system of claim 21 wherein at least one of said semiconductor diodes is a distributed feedback laser.

23. The system of claim 12 wherein said illumination arrangement includes a first laser and a second laser for generating said first laser energy and said second laser energy, respectively, such that the first laser energy and the second laser energy are incident on the source arrangement as said source laser energy and said first light path offsets the first laser to produce the first light path laser energy such that the first light path laser energy is incident on said detection arrangement, as one part of said detector laser energy, and a second light path from the second laser to the detection arrangement such that the second laser energy is incident on the detector arrangement, as said second light path energy and thereby forming another part of said detector laser energy.

24. The system of claim 23 wherein said first light path includes a selected one of a phase modulator and a frequency shifter for producing the offset of said first light path laser energy from the first laser energy at an offset frequency.

25. The system of claim 23 wherein said first laser energy, said second laser energy and said first light path laser energy each include a phase fluctuation characteristic that is correlated with one another and said detector arrangement uses said detector laser energy and said subcentimeter radiation in a way which causes said phase noise to cancel, at least to a limited extent, with respect to said electrical output signal.

26. The system of claim 25 wherein said laser illumination arrangement includes a mode locked laser for producing an output frequency comb and an arrangement for locking said first and second lasers to the frequency comb of the mode locked laser such that said phase fluctuation characteristic is correlated between the first laser energy, the second laser energy and the first light path laser energy.

27. The system of claim 12 wherein said laser illumination arrangement includes (i) a first laser for use in producing said first laser energy, (ii) a sweep oscillator for producing a given frequency sweep, and (iii) a first offset phase locked loop for controlling the first laser using said given frequency sweep such that the first laser contributes the given frequency sweep to said first laser energy.

28. The system of claim 27 including a mode locked laser for producing a frequency comb that exhibits a plurality of modes and a second laser for cooperating with the first laser to produce the first laser energy and the second laser energy, and a second offset phase locked loop where the first laser is phase locked to a given mode of the mode locked laser by the first offset phase locked loop and the second laser is phase locked to a different mode of the mode locked laser and the first laser is swept relative to the given mode of the mode locked laser by the first offset phase locked loop.

29. The system of claim 27 wherein the second offset phase locked loop is configured to cooperate with the mode locked laser to provide an overall frequency sweep that is greater than the given frequency sweep.

30. The system of claim 29 wherein said mode locked laser includes a comb spacing at a comb spacing frequency and said illumination arrangement is configured for cooperatively adjusting the sweep oscillator and the second offset phase locked loop during the frequency sweep, to avoid a region of ambiguity at one-half of said comb spacing.

31. The system of claim 29 wherein the first offset phase locked loop is further configured to cooperate with the mode locked laser to sequentially use one or more other modes of the mode locked laser to further increase said overall frequency sweep.

32. The system of claim 1 wherein said laser illumination arrangement is configured for causing said sample influenced radiation, in the predetermined arrangement, to reflect from the sample.

33. The system of claim 1 wherein said laser illumination arrangement is configured for causing said sample influenced radiation, in the predetermined arrangement, to pass through said sample with the detector arrangement in a spaced apart relationship from the source arrangement.

34. The system of claim 1 wherein said detector frequency response of the detector arrangement is customized by using a detector body with an integrally formed antenna.

35. The system of claim 34 wherein said first light path includes a selected one of a phase modulator and a frequency shifter for producing the offset of the corresponding optical component of the detector laser energy at an offset frequency and said antenna is configured for generating the offset frequency as an electrical bias voltage that is present across the detector body.

36. A method for investigation of a sample, said method comprising:
providing a source arrangement having a source frequency response;
placing a detector arrangement in a positional relationship with said source arrangement such that said sample is located in relation to the source arrangement and the detector arrangement, and said detector arrangement having a detector frequency response; and
configuring a laser illumination arrangement for generating
(i) a source laser energy that is produced by at least two lasers that are offset phase locked with respect to one another and which source laser energy is incident on said source arrangement, based on the source frequency response, in a way which causes the source arrangement to emit subcentimeter radiation, at least a portion of which subcentimeter radiation interacts with said sample and the source laser energy interacts to produce a frequency sweep in the subcentimeter radiation and, thereafter, at least some of said portion of the subcentimeter radiation serves as a sample influenced radiation that is incident on the detector arrangement, based on said positional relationship, and
(ii) a detector laser energy that is incident on said detector arrangement and offset phase locked with the source laser energy in a way which produces at least one optical component of the detector laser energy that is offset with respect to a corresponding optical component of the source laser energy so that the detector laser energy and the sample influenced radiation interact, based on said detector frequency response, in a way which at least generates an electrical output signal across the detector arrangement such that the electrical output signal is responsive to the sample influenced radiation including said frequency sweep.

37. An apparatus for detecting a subcentimeter radiation, said apparatus comprising:
a detector having a detector arrangement with a detector frequency response having said subcentimeter radiation incident on the detector arrangement; and
an illumination arrangement for continuously illuminating the detector arrangement with laser radiation that is produced by at least two continuous wave lasers that are offset phase locked with respect to one another and at least one of which lasers provides a light output that includes a frequency sweep for causing the detector arrangement to respond, based on said detector frequency response and said frequency sweep, in a way which causes the laser radiation to interact with the subcentimeter radiation to produce a frequency downconverted signal from the subcentimeter radiation.

38. A system for investigation of a sample, said system comprising:
a source arrangement having a source with a source frequency response;
the apparatus of claim 37 having said detector arrangement in a positional relationship with said source arrangement such that said sample is located in relation thereto and said illumination arrangement is configured for producing said laser radiation including
(i) a source laser energy that is produced by at least two lasers that are offset phase locked with respect to one another and which source laser energy is incident on the source arrangement, based on the source frequency response, in a way which causes the source arrangement to emit said subcentimeter radiation, at least a portion of which subcentimeter radiation interacts with said sample and the source laser energy interacts to produce a frequency sweep in the subcentimeter radiation and, thereafter, at least some of said portion of the subcentimeter radiation serves as a sample influenced radiation that is incident on the detector arrangement, based on said positional relationship, and
(ii) a detector laser energy that is incident on said detector arrangement and offset phase locked with the source laser energy in a way which produces at least one optical component of the detector laser energy that is offset with respect to a corresponding optical component of the source laser energy so that the detector laser energy and the sample influenced radiation interact, based on said detector frequency response, in a way which at least generates an electrical output signal across the detector arrangement such that the electrical output signal is responsive to the sample influenced radiation including said frequency sweep.

39. The apparatus of claim 37 including using a photoconductive switch as said detector arrangement.

40. The apparatus of claim 39 wherein said photoconductive switch includes LTG ErAs/GaAs.

41. A method for detecting a subcentimeter radiation, said method comprising:

providing a detector with a detector frequency response having said subcentimeter radiation incident on the detector; and configuring an illumination arrangement for continuously illuminating the detector arrangement with laser radiation that is produced by at least two continuous wave lasers that are offset phase locked with respect to one another and at least one of which lasers provides a light output that includes a frequency sweep for causing the detector arrangement to respond, based on said given frequency response and said frequency sweep, in a way which causes the laser radiation to interact with the subcentimeter radiation to produce a frequency down-converted signal from the subcentimeter radiation.

* * * * *